United States Patent [19]

Blume et al.

[11] 4,391,805

[45] Jul. 5, 1983

[54] 1-(1,3-DIOXOLAN-2-YLMETHYL)-AZOLES, THEIR SALTS AND THEIR USE

[75] Inventors: Ernst Blume, Bad Soden am Taunus; Wolfgang Schaper, Frankfurt am Main; Wolfgang Raether, Dreieich; Walter Dittmar, Hofheim am Taunus, all of Fed. Rep. of Germany

[73] Assignee: Hoechst Aktiengesellschaft, Frankfurt am Main, Fed. Rep. of Germany

[21] Appl. No.: 311,184

[22] Filed: Oct. 14, 1981

[30] Foreign Application Priority Data

Oct. 16, 1980 [DE] Fed. Rep. of Germany ....... 3039087

[51] Int. Cl.³ .................. A61K 31/415; C07D 405/06
[52] U.S. Cl. ................ 424/246; 424/248.58; 424/250; 424/258; 424/267; 424/269; 424/273 R; 424/273 P; 544/60; 544/132; 544/58.7; 544/139; 544/366; 544/370; 546/144; 546/164; 546/210; 548/262; 548/336
[58] Field of Search ................ 544/58.7, 60, 132, 139, 544/366, 370; 546/144, 164, 210; 548/262, 336; 424/246, 248.58, 250, 258, 267, 269, 273 R, 273 P

[56] References Cited

U.S. PATENT DOCUMENTS 4,160,841 7/1979 Heeres et al. .................. 424/273 R
4,223,036 9/1980 Heeres et al. ...................... 424/269

OTHER PUBLICATIONS

Heeres et al., Journ. Med. Chem. 22, 1003–1005, (1979).

Primary Examiner—Richard Raymond
Attorney, Agent, or Firm—Curtis, Morris & Safford

[57] ABSTRACT 1-(1,3-Dioxolan-2-ylmethyl)-azoles of the general formula

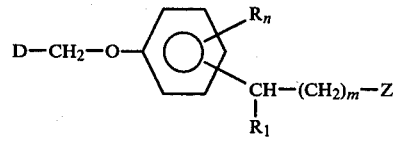

and their stereoisomers and their salts with physiologically acceptable acids, the preparation of these compounds, pharmaceutical formulations containing the latter and their use against mycoses, protozoa and Gram-positive and Gram-negative bacteria are described.

13 Claims, No Drawings

1-(1,3-DIOXOLAN-2-YLMETHYL)-AZOLES, THEIR SALTS AND THEIR USE

The invention relates to 1-(1,3-dioxolan-2-ylmethyl-)azoles their salts processes for their preparation and their use against fungalinfections.

U.S. Pat. Nos. 3,936,470; 853,726; 4,101,664; 4,101,665; 4,101,666 and 4,156,008, Belgian Patent Specifications Nos. 835,579 and 837,831, German Offenlegungsschriften Nos. 2,602,770; 2,803,870; 2,804,096; 2,930,029 and 2,930,196 and European Patent Application No. 0,007,696 describe 1-(1,3-dioxolan-2-ylmethyl)-1H-imidazoles and 1-(1,3-dioxolan-2-ylmethyl)-1H-1,2,4-triazoles for combating fungi and bacteria; however, their action and toleration are not always entirely satisfactory. The compounds according to the invention differ from these compounds essentially in the nature of the substituents in the 4-position of the dioxolane group.

It is the oject of the invention to provide 1-(1,3-dioxolan-2-ylmethyl)-azole derivatives of the formula (I)

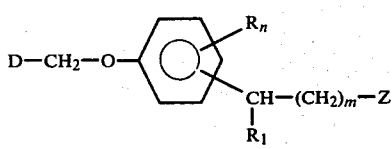

and their stereoisomers and their salts with a physiologically compatible acid, in which D denotes a 1-(1,3-dioxolan-2-ylmethyl)-azole radical of the following structure

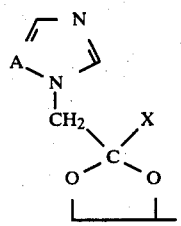

in which in turn A denotes nitrogen or methine and X denotes naphthyl, thienyl, halogenothienyl or a phenyl group optionally carrying 1, 2 or 3 sbstituents, the substituents being identical or different and denoting halogen, trifluoromethyl, $C_1$-$C_4$-alkyl or $C_1$-$C_4$-alkoxy, and, in formula (I) further the $R_n$'s, independently of one another denote halogen, trifluoromethyl, $C_1$-$C_8$-alkyl, $C_1$-$C_4$-alkoxy, $C_3$-$C_5$-alkenyl, $C_1$-$C_4$-alkoxycarbonyl, carboxyl, di-($C_1$-$C_4$)-alkylaminomethyl or nitro, n is 0, 1, 2 or 3, or in the event that n is 2, $R_n$ denotes a $C_4H_4$ radical which, together with the phenyl ring, forms a naphthyl ring, or in the event that n is 1, $R_n$ represents a phenoxy group optionally carrying 1 or 2 substituents, the substituents being identical or different and denoting halogen, trifluoromethyl, $C_1$-$C_4$-alkyl, preferably $C_1$-$C_2$-alkyl or $C_1$-$C_4$-alkoxy, preferably $C_1$-$C_2$-alkoxy, $R_1$ denotes hydrgen, $C_1$-$C_4$-alkyl or a phenyl group carrying 1 or 2 substituents, the substituents being identical or different and denoting halogen, trifluoromethyl, nitro, $C_1$-$C_4$-alkyl or $C_1$-$C_4$-alkoxy, m denotes 0, 1 or 2, Z denotes either (a) an amino radical of the formula Z(a)

in which $R_2$ and $R_3$ are identical or different and each denotes hydrogen, $C_1$-$C_8$-alkyl, $C_3$-$C_5$-alkenyl, $C_3$-$C_8$-cycloalkyl or a phenyl or benzyl group optionally carrying 1, 2 or 3 substituents, the substituents being identical or different and each denoting halogen, $C_1$-$C_4$-alkyl, $C_1$-$C_4$-alkoxy or trifluoromethyl, or one of the two radicals $R_2$ or $R_3$ denotes $C_1$-$C_5$-alkanoyl or $C_1$-$C_4$-alkoxycarbonyl, or (b) a radical of the formula Z(b)

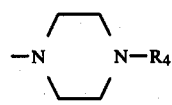

in which $R_4$ denotes hydrogen, $C_1$-$C_4$-alkyl, $C_3$-$C_5$-alkenyl, hydroxy-($C_2$-$C_3$)-alkyl, preferably hydroxyethyl, $C_1$-$C_4$-alkoxy-($C_2$-$C_3$)-alkyl, preferably $C_1$-$C_4$-alkoxyethyl, $C_1$-$C_5$-alkanoyl-, $C_2$-$C_5$-alkanoylmethyl, $C_1$-$C_4$-alkylsulfonyl, $C_1$-$C_4$-alkyloxycarbonyl, $C_1$-$C_4$-alkyloxycarbonylmethyl, mono-($C_1$-$C_4$)-alkylaminocarbonylmethyl, di-($C_1$-$C_4$)-alkylaminocarbonylmethyl, aminocarbonylmethyl-, $C_1$-$C_4$-alkylaminothiocarbonyl, $C_1$-$C_4$-alkylthiothiocarbonyl, aminocarbonyl, $C_3$-$C_5$-alkenylaminocarbonyl, preferably N-allylaminocarbonyl or $C_3$-$C_5$-alkenylaminothiocarbonyl, preferably N-allylaminothiocarbonyl, or $R_4$ denotes a phenyl-, phenylmethyl-, phenylaminocarbonyl-, phenylaminothiocarbonyl- or benzoyl group, each of the phenyl groups optionally carrying 1 or 2 substituents which are identical or different and denote halogen, trifluoromethyl, $C_1$-$C_4$-alkyl, in particular $C_1$-$C_2$-alkyl, or $C_1$-$C_4$-alkoxy, in particular $C_1$-$C_2$-alkoxy, or (c) a 1-H-imidazol-1-yl-, 1-H-1,2,4-triazol-1-yl-, pyrazol-1-yl-, pyrrolidin-1-yl-, piperidin-1-yl-, morpholin-4-yl-, thiomorpholin-4-yl-, 2,6-dimethylmorpholin-4-yl, 2,6-dimethylthiomorpholin-4-yl or 1,2,3,4-tetrahydroquinolin-1-yl or 1,2,3,4-tetrahydroisoquinolin-2-yl radical, or (d) an isocyano group of the formula Z(d)

or (e) an isothiocyano group of the formula Z(e)

or (f) a radical of the general formula Z(f)

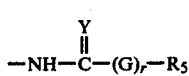

in which Y represents oxygen or sulfur, G represents oxygen or an NH group, r represents 0 or 1 and $R_5$ represents hydrogen, $C_1$-$C_4$-alkyl, monohalogenomethyl, dihalogenomethyl, trihalogenomethyl or a phenyl group optionally carrying 1 or 2 substituents, the substituents being identical or different and each denoting halogen, trifluoromethyl, $C_1$–$C_4$-alkyl, in particular $C_1$–$C_2$-alkyl, or $C_1$–$C_4$-alkoxy, in particular $C_1$–$C_2$-alkoxy, subject to the proviso that, in the event that Y represents a sulfur atom, G denotes a NH group and r denotes the number 1, that, in the event that G represents an oxygen atom and r represents the number 1, $R_5$ does not denote hydrogen, and that, in the event that $R_5$ represents monohalogenomethyl, dihalogenomethyl or trihalogenomethyl, r denotes 0 and Y oxygen.

Surprisingly, the 1-(1,3-dioxolan-2-ylmethyl)-azoles according to the invention exhibit a better and broader antimycotic activity than the known 1-(1,3-dioxolan-2-ylmethyl)-1H-imidazoles and 1-(1,3-dioxolan-2-ylmethyl)-1H-1,2,4-triazoles and than 2-S, (R)-(2,4-dichlorophenyl)-2-(imidazol-1-ylmethyl)-4-R,(S)-[4-(4-acetylpiperazin-1-yl)phenoxymethyl]-1,3-dioxolane (Ketoconazol).

In this context the term "halothienyl radical" is to be understood as meaning a thienyl radical which is linked in the 2-position or 3-position and which can be substituted in any desired position by a halogen atom, preferably bromine or chlorine, the term "$C_1$–$C_4$-alkyl" is to be understood as meaning an unbranched or branched hydrocarbon radical having 1-4 carbon atoms, such as, for example, the methyl, ethyl, propyl, 1-methylethyl, butyl, 2-methylpropyl or 1,1-dimethylethyl radical, the term "$C_1$–$C_8$-alkyl" is to be understood as meaning an unbranched or branched hydrocarbon radical having 1-8 carbon atoms, such as, for example, the radicals mentioned above or a pentyl, hexyl, heptyl, octyl or 1,1-dimethyl-3,3-dimethylbutyl group, the term "$C_3$–$C_8$-cycloalkyl" is to be understood as meaning an unbranched cyclic hydrocarbon having 3-8 carbon atoms, "$C_1$–$C_4$-alkoxy" is to be understood as meaning an alkoxy group in which the hydrocarbon radical has the meaning indicated unter the term "$C_1$–$C_4$-alkyl", the term "$C_1$–$C_5$-alkanoyl" is to be understood as meaning an unbranched or branched alkanoyl radical having 1-5 carbon atoms, such as the formyl, acetyl, propanoyl, 2-methylpropanoyl, butanoyl, 2-methylbutanoyl and 2,2-dimethylpropanoyl groups, the term "$C_3$–$C_5$-alkenyl" is to be understood as meaning an unbranched or branched alkene radical having 3-5 carbon atoms, such as, for example, the prop-1-en-3-yl-, 3-methylprop-1-en-3-yl, 1-methylprop-1-en-3-yl, 1,1-dimethylprop-1-en-3-yl, but-1-en-4-yl, pent-1-en-5-yl radical, and the term "halogen" is to be understood as meaning a fluorine, chlorine, bromine or iodine atom.

Preferred compounds of the general formula (I) are those in which X denotes a phenyl group which is unsubstituted or substituted by 1 or 2 halogen atoms or by a methyl, methoxy or trifluoromethyl radical, or denotes a thienyl group which is unsubstituted or monosubstituted by halogen, halogen preferably denoting, as above, fluorine, chlorine or bromine, or X denotes a naphthyl group.

Amongst the compounds of the general formula (I) for which n is >1, those in which $R_n$ has identical or different meanings and denotes halogen, in particular chlorine or bromine, $C_1$–$C_4$-alkyl or $C_1$–$C_4$-alkoxy radicals are preferred.

Amongst the compounds of the general formula (I) for which m is >0, those for which $R_1$ represents a hydrogen atom are preferred.

Compounds of the general formula (I) which are more strongly preferred are those in which X denotes a phenyl group which is substituted by 1 or 2 halogen atoms, preferably fluorine, chlorine or bromine, or denotes a trifluoromethylphenyl, 4-methylphenyl or 4-methoxyphenyl group, n is <3 and m is $\leq 1$, $R_1$ preferably denoting hydrogen if m=1.

Compounds of the general formula (I) which are most strongly preferred are those in which X represents a 4-fluorophenyl, 4-chlorophenyl, 4-bromophenyl, 4-trifluoromethylphenyl or 2,4-dichlorophenyl radical, in particular a 2,4-dichlorophenyl or 4-chlorophenyl group, the $R_n$'s independently of one another, denote halogen, $C_1$–$C_4$-alkyl, methoxy, allyl, n is 0 or 2, $R_1$ denotes hydrogen, m=0 and A is a methine group, while Z denotes either (a) an amino radical of the formula Z(a)

in which $R_2$ and $R_3$ are identical or different and denote hydrogen, $C_1$–$C_8$-alkyl, allyl, $C_3$–$C_8$-cycloalkyl or a phenyl or benzyl group optionally carrying 1 or 2 substituents, the substituents being identical or different and each denoting halogen, $C_1$–$C_4$-alkyl, $C_1$–$C_4$-alkoxy or trifluoromethyl, or one of the two radicals $R_2$ or $R_3$ denotes $C_1$–$C_5$-alkanoyl, or (b) a radical of the formula Z(b)

in which $R_4$ denotes hydrogen, $C_1$–$C_4$-alkyl, allyl, $C_1$–$C_5$-alkanoyl, methylsulfonyl, methoxycarbonyl, or $C_1$–$C_4$-alkylaminocarbonyl or $R_4$ denotes a phenyl, phenylmethyl, or benzoyl group, each of the phenyl groups optionally carrying 1 or 2 substituents which are identical or different and denote halogen, trifluoromethyl, $C_1$–$C_4$-alkyl, in particular $C_1$–$C_2$-alkyl, or $C_1$–$C_4$-alkoxy, in particular $C_1$–$C_2$-alkoxy, or (c) a piperidin-1-yl-, morpholin-4-yl, 2,6-dimethylmorpholin-4-yl, thiomorpholin-4-yl-, 2,6-dimethylthiomorpholin, (d) a radical of the formula Z(f)

in which Y represents oxygen, r represents 0, and $R_5$ represents $C_1$–$C_4$-alkyl, or a phenyl group optionally carrying 1 or 2 substituents, the substituents being identical or different and each denoting halogen, trifluoromethyl, $C_1$–$C_4$-alkyl, in particular $C_1$–$C_2$-alkyl, or $C_1$–$C_4$-alkoxy, in particular $C_1$–$C_2$-alkoxy.

The compounds of the formula (I) can be prepared by the process described as follows.

The first process for the preparation of the compounds of the formula (I) comprises reacting a compound of the formula (II)

in which D has the meaning indicated above and E denotes a reactive ester radical, with a compound of the formula (III)

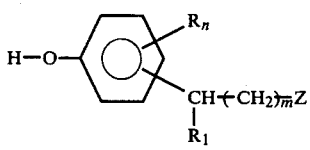 (III)

in which $R_n$, $R_1$, m and Z have the meanings indicated above, and, if appropriate, acylating or alkylating, if desired in the presence of carbon disulfide, the compounds of the formula (I) thus obtained.

The second process for the preparation of compounds of the formula (I) comprises first reacting a compound of the formula (IV)

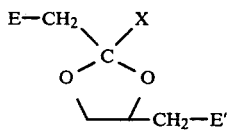 (IV)

in which X has the meaning indicated above and E or E' has the meaning indicated above for the formula (II) for E, with a compound of the general formula (III), and thus preparing a compound of the formula (V)

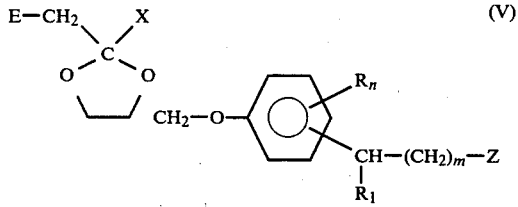 (V)

in which X, $R_n$, $R_1$, m and Z have the meanings indicated above and E has the meaning indicated for the formula (II), and subsequently reacting a compound of the formula (V) with a compound of the formula (VI)

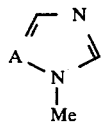 (VI)

in which A has the meaning indicated above and Me denotes hydrogen or a metal atom, and, if appropriate, acylating or alkylating, if desired in the presence of carbon disulfide, the compounds of the formula (I) thus obtained.

The third process for the preparation of compounds of the formula (I) comprises reacting a compound of the formula (VII)

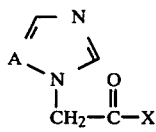 (VII)

in which A and X have the meanings indicated above, with a 1,2-diol of the general formula (VIII)

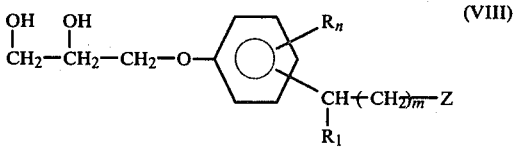 (VIII)

in which $R_n$, $R_1$, m and Z have the meanings indicated for the formula (I), or carrying out the reaction with the corresponding epoxide, and, if appropriate, acylating or alkylating, if desired in the presence of carbon disulfide, a compound of the formula (I) thus obtained.

The first process is carried out by reacting a compound of the general formula (II)

$$D—CH_2—E \qquad (II)$$

in which D has the meaning indicated for the formula (I) and E denotes a reactive ester radical, such as methylsulfonyloxy, phenylsulfonyloxy, 4-methylphenylsulfonyloxy, 4-chlorophenylsulfonyloxy, trifluoromethylsulfonyloxy, trifluoroacetoxy or halogen, in particular chlorine, bromine or iodine, with a compound of the general formula (III)

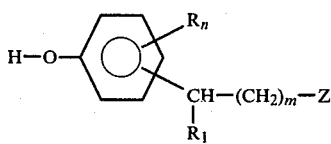 (III)

in which $R_n$, $R_1$, m and Z have the meanings indicated for formula (I) in claim 1.

The reaction mentioned above is carried out within a temperature range from 30° to 150° C., preferably 40° to 100° C., in the presence of a base and in an inert organic solvent, such as N,N-dimethylformamide, N,N-dimethylacetamide, dimethyl sulfoxide, N-methyl-2-pyrrolidone, dioxane, tetrahydrofuran, 4-methyl-2-pentanone, methanol, ethanol, isopropyl alcohol, propanol, butanol, pentanol, tert.-butyl alcohol, methylglycol, methylene chloride or an aromatic hydrocarbon, such as benzene, chlorobenzene, toluene or xylene, or in water. It is also possible to use mixtures of the solvents mentioned as examples.

Examples of suitable bases are alkali metal carbonates, bicarbonates, hydroxides, alcoholates or hydrides or alkaline earth metal carbonates, bicarbonates, hydroxides, alcoholates or hydrides, such as, for example, sodium carbonate, sodium bicarbonate, potassium carbonate, sodium hydroxide, sodium methylate or sodium hydride, or organic bases, for example tertiary amines, such as triethylamine, tributylamine, ethylmorpholine, pyridine, dimethylaminopyridine, quinoline, 1,5-diazabicyclo[5,4,0]-undec-5-ene-(1,8-7) (DBU), 1-H-imidazole or 1-H-1,2,4-triazole.

The reaction is also carried out under the conditions of a phase transfer reaction, in which the reactants are allowed to act upon one another within a temperature range of from 20° to 120° C. in one of the above solvents, while stirring vigorously and in the presence of a phase transfer catalyst and either a powdered alkali metal hydroxide, such as, for example, sodium hydroxide or potassium hydroxide, or a concentrated aqueous solution thereof.

Examples of suitable phase transfer catalysts are trialkylbenzylammonium halides, hydroxides or bisulfates or tetraalkylammonium halides, hydroxides or bisulphates having preferably 1 to 12 C-atoms in the alkyl radical, or crown ethers, such as for example, 12-crown-4, 15-crown-5, 18-crown-6 or dibenzo-18-crown-6.

If in the formula (I) mentioned above, the radical Z denotes an amino radical of the general formula Z(a) in claim 1, in which at least one of the radicals $R_2$ or $R_3$ represents a hydrogen atom, but none of the radicals represents a $C_1$-$C_5$-alkanoyl or $C_1$-$C_4$-alkoxycarbonyl group (compare formula (Ia-2) below) or an unsubstituted 1-piperazinyl group (compare formula (I-b) below), it is advantageous to employ, in the first process of preparation mentioned above, a phenol of the general formula (III) in which the free amino or piperazinyl group is protected by an appropriate protective group Sg (compare formulae (III-a) and (III-b) below). This prevents N-alkylation. The protective group Sg is split off by alkaline hydrolysis from the compounds thus obtained (compare formulae (Ia-1) and (Ia-3) below). Examples of suitable protective groups are $C_1$-$C_4$ alkanoyl, in particular formyl, acetyl or trifluoroacetyl, or $C_1$-$C_4$ alkoxycarbonyl, in particular the methoxycarbonyl radical.

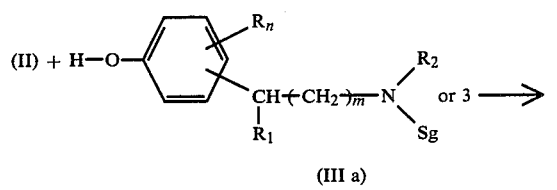

(III a)

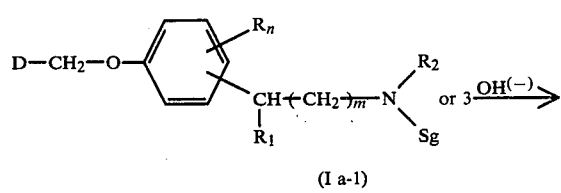

(I a-1)

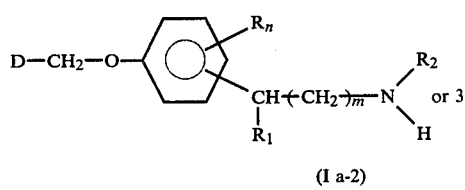

(I a-2)

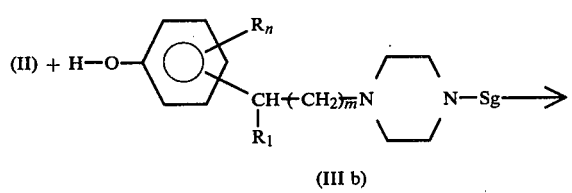

(III b)

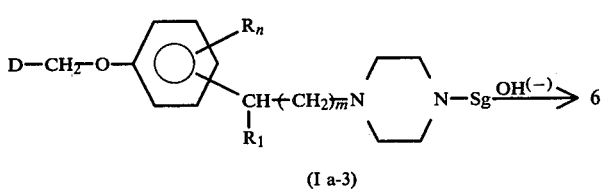

(I a-3)

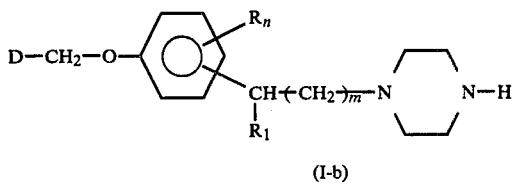

(I-b)

A compound of the formula (I) obtained in this way, which contains one or two hydrogen atoms in the substituents Z, in the form of Z(a) or Z(b) in claim 1 (compare formulae (Ia-2) and (Ib)), is, if appropriate, acylated with a customary acylating agent or is alkylated with a customary alkylating agent, if desired in the presence of carbon disulfide.

Thus a compound of the general formula (Ib)

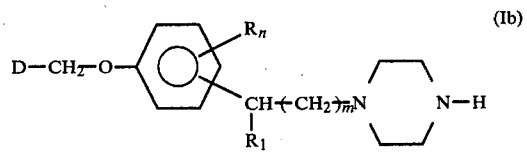

in which D, $R_n$, $R_1$ and m have the above meanings, is preferably reacted, if appropriate in the presence of a base, with a compound of the general formula (IX)

$$R_6-N=C=Y \qquad (IX)$$

in which Y denotes oxygen or sulfur and $R_6$ has the meanings mentioned in connection with formula (Ic), to give a compound of the general formula (Ic)

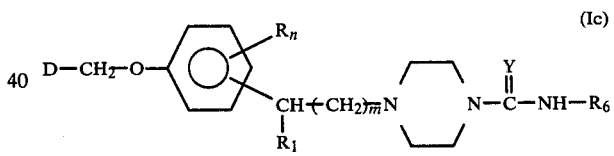

in which D, $R_1$, $R_n$ and m have the meanings indicated in claim 1, Y represents oxygen or sulfur, and $R_6$ denotes hydrogen, $C_3$-$C_5$ alkenyl, $C_1$-$C_4$ alkyl or a phenyl group which optionally carries 1 or 2 substituents, the substituents being identical or different and denoting, in each case, halogen, trifluoromethyl, $C_1$-$C_4$ alkyl, preferably $C_1$-$C_2$ alkyl, or $C_1$-$C_4$ alkoxy, in particular $C_1$-$C_2$ alkoxy.

The above reaction is carried out with or without a solvent, preferably in an inert solvent, at elevated temperature and, if appropriate, in the presence of a base, as indicated above for the first process of preparation.

If $R_6$ represents hydrogen, it is appropriate to react a suitable alkali metal cyanate or thiocyanate with a compound of the general formula (Ib) or the hydrochloride thereof, in an organic acid, such as, for example, acetic acid, or an alcohol, such as, for example, ethanol, if appropriate with the addition of water, isocyanic or cyanic acid or thiocyanic acid (a compound of the general formula (IX) in which $R_6$ denotes hydrogen) being initially liberated from the alkali metal cyanate or thiocyanate.

Furthermore, a compound of the general formula (Id)

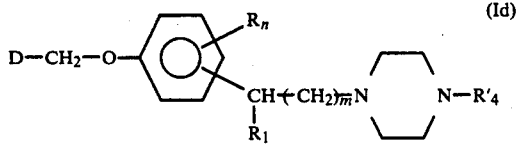

in which D, $R_n$, $R_1$ and m have the meanings indicated in claim 1 and $R_4'$ denotes a $C_1$-$C_5$ alkanoyl, monohalogenomethylcarbonyl, dihalogenomethylcarbonyl, trihalogenomethylcarbonyl, $C_1$-$C_4$ alkylsulfonyl, $C_1$-$C_4$ alkoxycarbonyl, $C_3$-$C_5$ alkenylaminocarbonyl, mono-($C_1$-$C_4$)-alkylaminocarbonyl, di-($C_1$-$C_4$)-alkylaminocarbonyl, phenoxycarbonyl, phenylaminocarbonyl or benzoyl radical, each of the phenyl groups optionally carrying 1 or 2 substituents which are identical or different and denote halogen or trifluoromethyl, $C_1$-$C_4$ alkyl, in particular $C_1$-$C_2$ alkyl, or $C_1$-$C_4$ alkoxy, preferably $C_1$-$C_2$ alkoxy, radicals, is preferably prepared by reacting a compound of the general formula (Ib), in the presence of a suitable base, in an inert solvent and within the temperature range from $-10°$ to $120°$ C., with an appropriate acyl halide derived from the corresponding carboxylic or sulfonic acid, in the case of $C_2$-$C_5$ carboxylic acids, in particular, also employing their anhydrides as acylating agents.

The solvents and bases used are preferably those mentioned for the first process of preparation.

If $R_4'$ denotes a formyl group, the acylation is carried out by means of formic acid, preferably by means of formic acid methyl or ethyl ester. If $R_4'$ represents a $C_1$-$C_4$ alkoxycarbonyl radical or a phenoxycarbonyl radical, an appropriate ester of carbonic acid is employed as the acylating agent.

Furthermore, a compound of the general formula (Id')

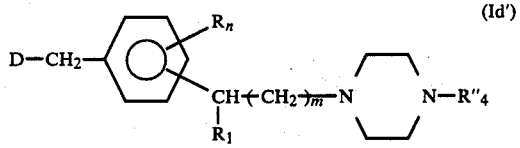

in which D, $R_n$, $R_1$ and m have the meanings indicated in claim 1 and $R_4''$ represents $C_1$-$C_4$ alkyl, $C_2$-$C_5$ alkanoylmethyl, hydroxy-($C_2$-$C_3$)-alkyl, in particular hydroxyethyl, $C_1$-$C_4$ alkoxycarbonylmethyl, aminocarbonylmethyl, $C_1$-$C_4$ alkylaminocarbonylmethyl or phenylmethyl, it being possible for the phenyl group optionally to carry 1 or 2 substituents which, independently of one another, denote halogen, $C_1$-$C_4$ alkyl, in particular $C_1$-$C_2$ alkyl, or $C_1$-$C_4$ alkoxy, preferably $C_1$-$C_2$ alkoxy, is preferably prepared by alkylating a compound of the general formula (Ib) with a compound of the general formula (X)

E—$R_4''$     (X)

in which E has the meanings indicated for the formula (II) and $R_4''$ has the above meanings. The alkylation is preferably carried out in an inert solvent, in the presence of a base such as those listed for the first process of preparation, and within a temperature range from 20° to 120° C.

Those compounds of the general formula (Id') in which $R_4''$ represents a hydroxyethyl radical are preferably prepared by reacting a compound of the general formula (Ib) with ethylene oxide, for example by passing the latter into a hot solution of the compound of the general formula (Ib) in an organic solvent which is listed for the first process of preparation, or a compound of the general formula (Ib) is heated with ethylene carbonate, preferably at 50°-150° C., and, if appropriate, with the addition of an alkali metal carbonate, such as, for example, sodium carbonate, undiluted or, preferably, in an inert organic solvent, as listed for the first process of preparation, for example dimethylformamide.

Those compounds of the general formula (Id') in which $R_4''$ denotes $C_1$-$C_4$ alkoxy-($C_2$-$C_3$)-alkyl, in particular $C_1$-$C_4$ alkoxyethyl, are preferably prepared from the compounds of the general formula (Id') described above in which $R_4''$ denotes hydroxyethyl, by alkylation with a compound of the general formula (X) in which E has the meanings indicated for the formula (II) and $R_4''$ denotes $C_1$-$C_4$ alkyl. The alkylation is preferably carried out in an inert solvent, in the presence of a base such as is listed for the first process of preparation, and within a temperature range from 20° to 120° C.

Those compounds of the general formula (Id') in which $R_4''$ represents either a $C_1$-$C_4$ alkyl group or a phenylmethyl group carrying 1 or 2 substituents on the phenyl nucleus, the substituents having the above meanings, are preferably prepared by reductive amination from a compound of the general formula (Ib) and an aldehyde or ketone, by treating the reactants with hydrogen in an inert solvent, for example an alcohol as mentioned for the first process of preparation, and in the presence of a hydrogenation catalyst, such as, for example, palladium-on-wood charcoal, and a base, such as, for example, sodium acetate, or catalytic quantities of an acid, such as, for example, acetic acid, hydrochloric acid, phosphoric acid or sulfuric acid. The reaction is preferably carried out under normal pressure or up to 150 atmospheres gauge and within a temperature range between 20° and 150° C.

Those compounds of the general formula (Id') in which $R_4''$ denotes a $C_1$-$C_4$ alkylaminocarbonylmethyl radical are preferably prepared from the corresponding compounds of the general formula (Id') in which $R_4''$ represents a $C_1$-$C_4$ alkoxycarbonylmethyl group, by reacting the last mentioned compounds at 20°-150° C. with a $C_1$-$C_4$ alkylamine, in bulk or, advantageously, in a solvent indicated for the first process of preparation.

Furthermore, a compound of the general formula (Ie)

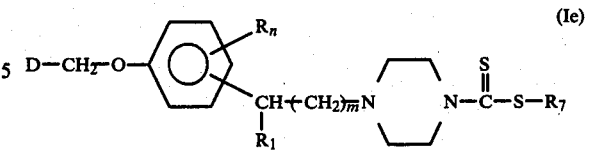

in which D, $R_n$, $R_1$ and m have the meanings indicated in claim 1 and $R_7$ denotes a $C_1$-$C_4$ alkyl radical, is preferably prepared by alkylating a compound of the general formula (Ib), in a solvent and in the presence of a base and carbon disulfide, with a compound of the general formula (X) in which E has the meanings indicated for the formula (II) and $R_4''$ denotes $C_1$-$C_4$ alkyl. The bases, solvents and reaction conditions used are indicated for the first process of preparation.

Furthermore, a compound of the general formula (If)

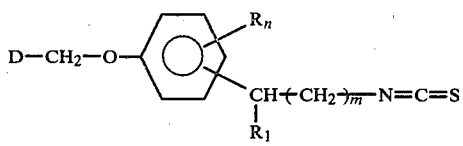

in which D, $R_n$, $R_1$ and m have the meanings indicated in claim 1, is preferably prepared by converting a compound of the general formula (Ia-4)

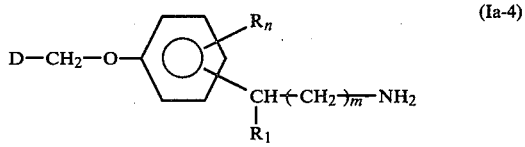

in which D, $R_n$, $R_1$ and m have the meanings indicated in claim 1, into the isothiocyanate of the general formula (If).

This is effected either by reacting a compound of the general formula (Ia-4) which thiophosgene in an inert solvent and in the presence of a base such as is mentioned for the first process of preparation, or acylating this compound in the presence of carbon disulfide, in which case it is appropriate to use carbodiimides or chloroformic acid esters.

Thus, for example, a compound of the general formula (Ia-4) is reacted with carbon disulfide either in pyridine together with N,N'-dicyclohexylcarbodiimide, or in methylene chloride in the presence of triethylamine together with chloroformic acid methyl ester.

Furthermore, a compound of the general formula (Ig)

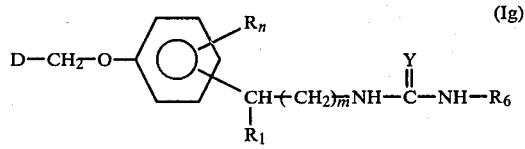

in which D, $R_n$, $R_1$, m and Y have the meanings indicated in claim 1 and $R_6$ has the meanings indicated for formula (Ic), is preferably prepared by reacting a compound of the general formula (Ia-4) with a compound of the general formula (IX)

$$R_6-N=C=Y \qquad (IX)$$

in which Y represents oxygen or sulfur and $R_6$ has the meanings indicated for the formula (Ic).

The reaction conditions are the same as those indicated above for the preparation of compounds of the formula (Ic) by reacting compounds of the formula (Ib) with compounds of the formula (IX).

Furthermore, a compound of the general formula (Ih)

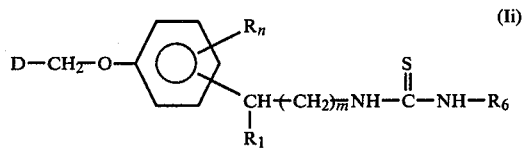

in which D, $R_n$, $R_1$, m, r and $R_5$ have the meanings indicated in claim 1, is preferably prepared by reacting a compound of the general formula (Ia-4) with an acylating agent.

Suitable acylating agents for the preparation of compounds of the general formula (Ih) in which r denotes the number 0 are acyl halides and anhydrides derived from the acid $R_5$—COOH, it being appropriate to use formic acid or, for example, formic acid ethyl ester for the case of formylation.

Suitable acylating agents for the preparation of compounds of the general formula (Ih) in which r denotes the number 1 are ester-chlorides of carbonic acid or di-$R_5$ carbonates wherein $R_5$ has the meaning indicated for the formula (Ih).

The reaction conditions are the same as those indicated above for the preparation of compounds of the formula (Id) by reacting compounds of the formula (Ib) with an acyl halide or anyydride.

Furthermore, a compound of the general formula (Ii)

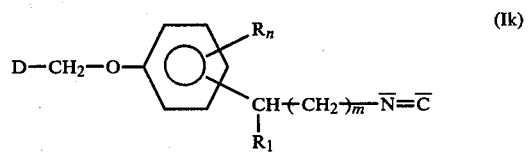

in which D, $R_n$, $R_1$ and m have the meanings indicated in claim 1, is preferably prepared by reacting a compound of the general formula (If) with an amine $R_6$—$NH_2$ in which $R_6$ has the meanings mentioned for formula (Ic).

The reaction conditions are the same as those indicated above for the preparation of compounds of the formula (Ic) by reacting compounds of the formula (Ib) with compounds of the formula (IX).

Furthermore, a compound of the general formula (Ik)

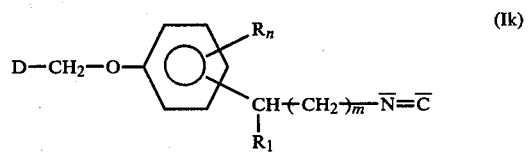

in which D, $R_n$, $R_1$ and m have the meanings indicated in claim 1, is preferably prepared by reacting a compound of the general formula (Ia-4) with chloroform or bromoform under the conditions of a phase transfer reaction (as described above), or by reacting a compound of the general formula (Ia-5)

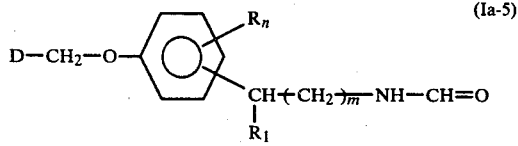 (Ia-5)

in which D, $R_m$, $R_1$ and m have the meanings indicated in claim 1, with an acylating agent, such as, for example, phosgene, thionyl chloride, phosphorus trichloride, phosphorus tribromide, phosphorus oxychloride, phosphorus pentachloride, phosphorus pentoxide, cyanuric chloride, benzenesulfochloride or toluenesulfochloride or with equimolar quantities of triphenylphosphine and carbon tetrachloride, in each case in the presence of a base and in an inert solvent, as indicated for the first process of preparation, and within a temperature range from $-50°$ to $+50°$ C.

Thus, for example, a compound of the general formula (Ia-5) is advantageously reacted with phosphorus oxychloride in methylene chloride in the presence of triethylamine.

PREPARATION OF THE STARTING MATERIALS

The Preparation of Compounds of the General Formula II

The starting compounds of the general formula (II) in which D has the meaning indicated in claim 1 and A denotes a methine group are described in Belgian Patent Specification No. 837,831, German Offenlegungsschrift No. 2,804,096 and in J.Med.Chem. 1979, 22, page 1,003; those in which A denotes nitrogen can be prepared in analogy with the literature references quoted above (compare also the equation on page 23).

The Preparation of Compounds of the General Formula (III)

Many starting compounds of the general formula (III) are known.

The phenols of the general formula (III) in which $R_n$ and $R_1$ have the meanings indicated in claim 1, Z denotes a radical of the general formula Z(a), Z(b) or Z(c) in claim 1 (described as Z' in the following text) and m is 0 are readily accessible phenol Mannich bases.

They are prepared by reacting an appropriate phenol with an aldehyde of the general formula (XI) and an amino compound of the general formula (XII) (compare in this connection H. Hellmann and G. Opitz, "α-Aminoalkylierung", Verlag Chemie Weinheim (1969)),

 (XI)

 (XII)

$R_1$ having the meanings indicated in claim 1 and Z' having the meanings indicated in claim 1 for formula Z(a), Z(b) or Z(c), in the above general formulae (XI) and (XII).

They are also prepared by transamination of the phenol Mannich bases described above by heating, preferably dimethylaminophenol or diethylaminophenol, Mannich bases with an amino compound of the general formula (XII), in which Z' has the above meanings, at 50° to 180° C. in bulk or, preferably, in an inert organic solvent as indicated for the first process of preparation.

The phenols of the general formula (III) in which m=0, n=0, $R_1$ has the meanings indicated in claim 1 and Z has the meaning of Z' in relation to the formula (XII) are preferably prepared by reductive amination of hydroxybenzaldehydes or corresponding hydroxyphenylketones by means of primary or secondary amines of the general formula (XII) in which Z' has the above meanings.

The reaction conditions in this case correspond to those described above for the synthesis of compounds of the general formula (Id') by reductive amination of compounds of the general formula (Ib) with aldehydes or ketones.

The phenols of the general formula (III) in which m=0, $R_1$ is not hydrogen and in other respects has the meanings indicated in claim 1 and Z has the meaning of Z' in relation to the formula (XI) are preferably prepared analogously to the methods described in Eur.J.Med. Chem. 1979, pages 227–245.

The phenols of the general formula (III) in which m denotes the number 1 or 2, $R_n$ and $R_1$ have the meanings indicated in claim 1 and Z has the meaning of Z' for the formula (XII) are appropriately prepared by reducing corresponding methoxyphenylalkylcarboxylic acid amides with a suitable reducing agent, such as, for example, lithium aluminum hydride. The methoxyphenylalkylamines thus formed are appropriately converted into phenols of the general formula (III) by ether scission by means of a strong acid, such as, for example, hydrobromic acid, or a methoxyphenylalkanol is converted, in a manner generally customary, into a reactive ester of the general formula (XIII)

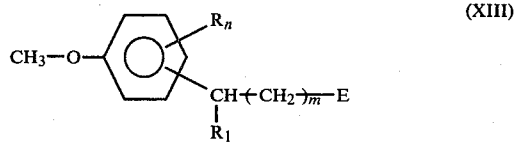 (XIII)

in which $R_n$ and $R_1$ have the meanings indicated in claim 1, E has the meanings indicated for the formula II and m denotes the number 1 or 2, and this ester is reacted with an amino compound of the general formula (XII) in which Z' has the meanings indicated for the formula Z(a), Z(b) or Z(c) in claim 1. The methoxyphenylalkylamine thus obtained is converted by ether scission as described above into a phenol of the general formula (III).

If the phenolic hydroxyl group interferes with the preparation of phenols of the general formula (III) in the syntheses described above, it is appropriate to block this group initially by means of a suitable protective group, which is later split off again. For example, the protected phenol can be employed in syntheses in the form of its methoxy compound, benzyloxy compound or acyloxy compound, and the methoxy compound can then be split by treatment with an appropriate strong acid, such as, for example, hydrobromic acid, or the benzyloxy compound can be split by hydrogenolysis using a catalyst, such as, for example, palladium-on-charcoal, and the acyloxy compound can be split by alkaline or acid hydrolysis, giving in each case the corresponding phenol.

The second process is carried out by first reacting a compound of the general formula (IV)

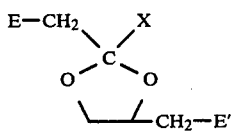

(IV)

in which X has the meanings indicated in claim 1 and E and E' have the meanings indicated for the formula (II) in claim 2, with a compound of the general formula (III) in claim 2, thus preparing a compound of the general formula (V)

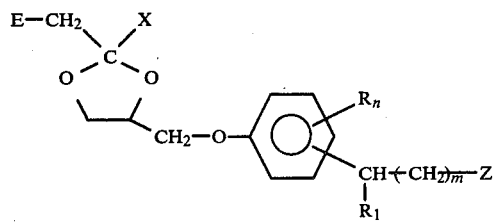

(V)

in which X, $R_n$, $R_1$, m and Z have the meanings indicated in claim 1 and E has the meanings indicated for the formula (II) in claim 2.

Compounds of the formula (I) are prepared in accordance with this process by subsequently reacting a compound of the general formula (V) with compounds of the general formula (VI)

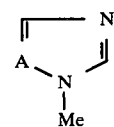

(VI)

in which A has the meaning indicated in claim 1 and Me denotes hydrogen or a metal atom.

The reaction conditions for the preparation of the compounds of the general formula (V) by reacting compounds of the general formula (IV) with compounds of the general formula (III) are the same as those indicated in the first preparative process for the preparation of compounds of the general formula (I) by reacting compounds of the general formula (II) with (III).

The preparation of compounds of the general formula (I) (in accordance with the second process) by reacting compounds of the general formula (V) with compounds of the general formula (VI) is preferably effected in an inert solvent, in the presence of a base, as indicated above for the first process of preparation, preferably within a temperature range from 100° to 190° C. The reaction is appropriately carried out in the presence of an alkali metal iodide, such as, for example, sodium iodide or potassium iodide, if appropriate in an autoclave under pressure.

The reactions described above are appropriately carried out as one-pot reactions by first reacting a compound of the general formula (IV) at 40° to 100° C. with a compound of the general formula (III) in the presence of a base and in an inert solvent. Without isolating the compound of the general formula (V), a compound of the general formula (VI) and, if appropriate, a further molar equivalent of a base and an alkali metal iodide (for example potassium iodide) are then added and the mixture is heated at 100° to 190° C.

A compound of the general formula (I) thus obtained, which contains one or two hydrogen atoms in the substituent Z in the form of Z(a) or Z(b) in claim 1 (compare formulae (Ia-2) and (Ib)), is optionally acylated by means of a customary acylating agent or is alkylated by means of a customary alkylating agent, if desired in the presence of carbon disulfide, as described in the first process of preparation according to claim 2.

PREPARATION OF THE STARTING MATERIALS

The Preparation of Compounds of the General Formula (IV)

Compounds of the general formula (IV) in which E and E' have the meanings indicated for E in relation to the general formula (II) are prepared by converting a compound of the general formula (XVI) (compare the reaction diagram below) into a reactive ester group in a customary manner.

Thus, for example, the compounds of the general formula (IV) (compare reaction diagram) in which E has the meanings indicated for the general formula (II) in claim 2 and E' denotes methylsulfonyloxy are prepared by reacting a compound of the general formula (XVI) in which X has the meanings indicated in claim 1 and E has the meanings indicated for the general formula (II), with methylsulfonyl chloride at −10° to +50° C. (compare reaction diagram below).

The above reaction is appropriately carried out in an inert solvent and in the presence of a base, as indicated for the first process of preparation.

The compounds of the general formula (IV) in which E' denotes chlorine or bromine are prepared, for example, by reacting compounds of the general formula (XVI) (compare reaction diagram below) with appropriate halogenating agents, such as, for example, thionyl chloride, phosphorus pentachloride or pentabromide or phosphorus oxychloride or oxybromide.

The above reaction is optionally carried out in an inert solvent, as indicated above for the first process of preparation, at 0° to 100° C.

Furthermore, compounds of the general formula (IV) in which E has the meanings indicated for the general formula (II) and E' denotes chlorine or bromine can be prepared by reacting a compound of the general formula (XIV) (compare reaction diagram) with 1-chloro-2,3-propanediol or 1-bromo-2,3-propanediol.

The reaction is carried out in an inert solvent, as indicated above in the case of the first process of preparation, in the presence of a suitable strong acid, such as, for example, 4-methylphenylsulfonic acid, benzenesulfonic acid, naphthalene-1,5-disulfonic acid, glacial acetic acid, sulfuric acid or phosphoric acid, within a temperature range from 80° to 180° C. It is advantageous to use a solvent mixture consisting of an inert solvent which forms an azeotropic mixture with water, such as, for example, benzene, toluene, xylene, chlorobenzene or cyclohexane, and an alcohol, as indicated above in the case of the first process of preparation.

The Preparation of Compounds of the General Formula (XVI)

Compounds of the general formula (XVI) in which X has the meanings indicated in claim 1 and E has the meanings indicated for the general formula (II) are prepared by reacting a compound of the general formula (XIV), in which X and E have the above meanings, with glycerol (compare reaction diagram below).

The reaction conditions are the same as those indicated above for the preparation of compounds of the general formula (IV) by reacting compounds of the general formula (XIV) with 1-chloro-2,3-propanediol.

Furthermore, compounds of the general formula (XVI) in which X has the meaning indicated in claim 1 and E denotes halogen, can be prepared by reacting a compound of the general formula (XV), in which X has the meaning indicated in claim 1, with glycerol, and reacting the compound thus obtained of the general formula (XVII) (compare reaction diagram below) with halogen, for example with bromine, in analogy with J.Med.Chem. 1979, 22, page 1003.

The 1st and 2nd processes of preparation are illustrated by means of the following reaction diagram.

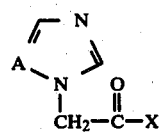

in which A and X have the meanings indicated in claim 1, with a compound of the general formula (VIII) or the corresponding epoxide of the general formula (VIII')

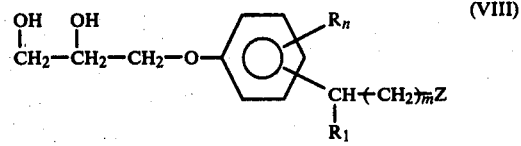

Reaction diagram

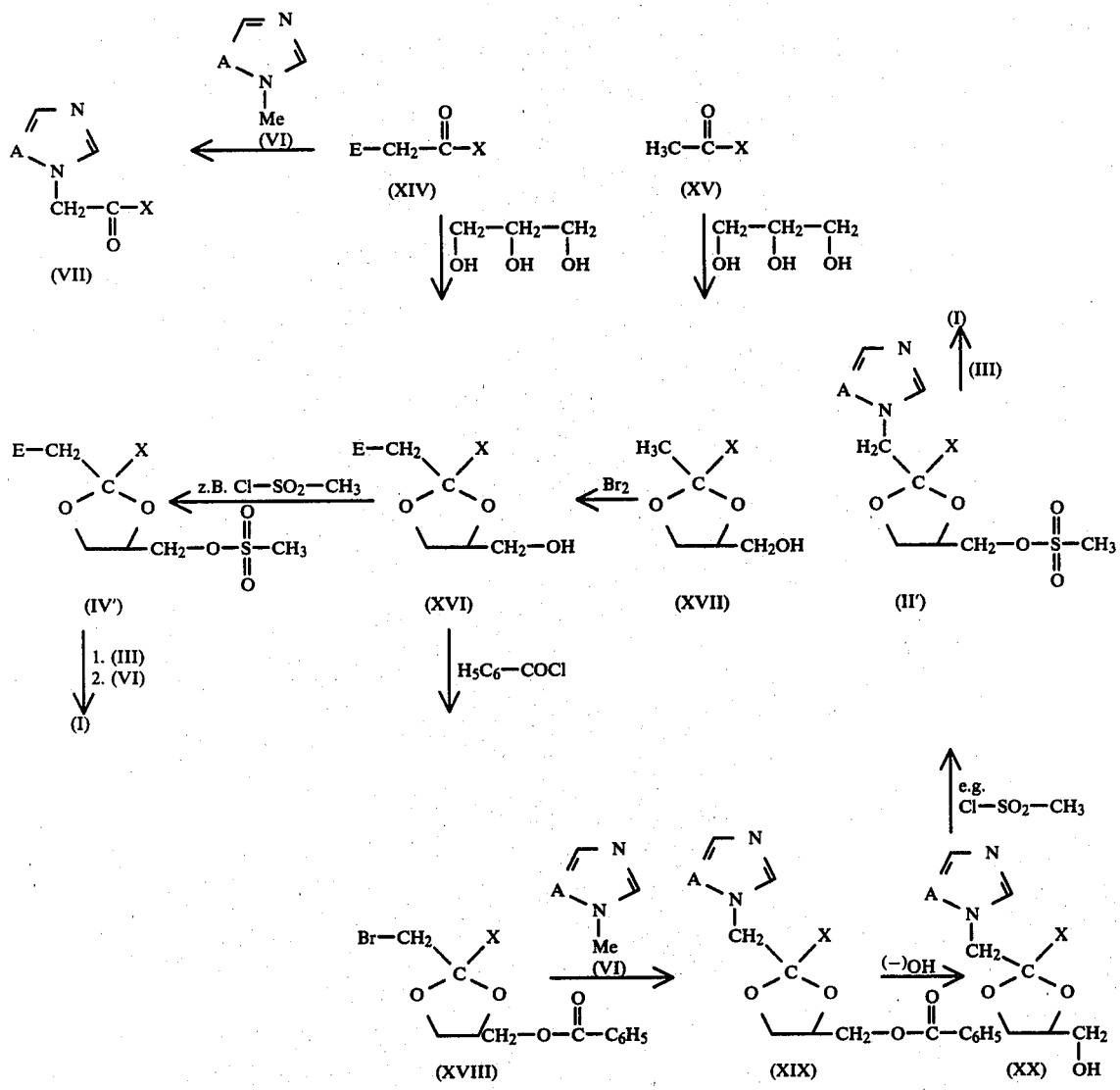

The third process is carried out by reacting a compound of the general formula (VII)

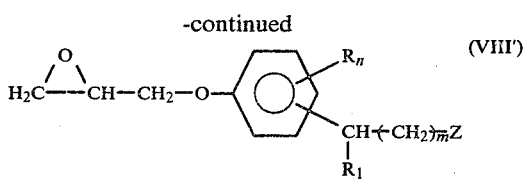

In the general formulae (VIII) and (VIII') above, $R_n$, $R_1$, m and Z have the meanings indicated in claim 1.

The reaction of compounds of the general formula (VII) with compounds of the general formula (VIII) is generally carried out under the same conditions as those described in the second process of preparation in the preparation of compounds of the general formula (IV) by reacting compounds of the general formula (XIV) with 1-chloro-2,3-propanediol. In the corresponding reaction of compounds of the general formula (VII) with compounds of the general formula (VIII'), it is appropriate to carry out the reaction in an inert solvent, as described in the first process of preparation, and in the presence of a suitable strong acid, as illustrated in the second process of preparation.

A compound of the general formula (I) thus obtained, which contains one or two hydrogen atoms in the substituent Z in the form of Z(a) or Z(b) in claim 1 (compare formulae (Ia-2) and (Ib)), is optionally acylated by means of a customary acylating agent or by means of a customary alkylating agent, if desired in the presence of carbon disulfide, as described in the first process of preparation according to claim 2.

PREPARATION OF THE STARTING MATERIALS

The preparation of compounds of the general formula (VII)

Insofar as they are not known, compounds of the general formula (VII) in which A and X have the meanings indicated in claim 1, are appropriately prepared by reacting compounds of the general formula (XIV) with (VI). The reaction is carried out in an inert solvent, if appropriate in the presence of a base and within a temperature range from $-10°$ to $+100°$ C. The bases and solvents used are indicated for the first process of preparation.

The preparation of compounds of the general formula (VIII)

Compound of the general formula (VIII) in which $R_n$, $R_1$, m and Z have the meanings indicated in claim 1 are prepared in a manner analogous to that described in Org. Synth. Collect. Vol. I, page 296, by reacting compounds of the general formula (III) with a 1-halogeno-2,3-propanediol.

THE PREPARATION OF COMPOUNDS OF THE GENERAL FORMULA (VIII')

Compounds of the general formula (VIII') in which $R_n$, $R_1$, m and Z have the meanings indicated in claim 1, can be prepared in a manner analogous to that described in J. Chem. Soc. 1954, page 1571, by reacting compounds of the general formula (III) with epichlorohydrin.

The compounds of the general formula (I) also exhibit their essential properties in the form of their salts. Any physiologically acceptable acids are suitable for the preparation of acid addition salts. These acids preferably include the hydrogen halide acids, such as, for example, hydrochloric and hydrobromic acid, as well as nitric acid and also phosphoric acid or sulfuric acid. Preferred organic acids are monofunctional and bifunctional carboxylic acids and hydroxycarboxylic acids, such as, for example, acetic acid, maleic acid, oxalic acid, succinic acid, fumaric acid, tartaric acid, citric acid, salicylic acid, sorbic acid, lactic acid and sulfonic acids, such as, for example, p-toluenesulfonic acid, methylsulfonic acid and phenylsulfonic acid and also 1,5-naphthalenedisulfonic acid. The salts of the compounds of the formula (I) can be obtained in a simple manner in accordance with customary methods of forming salts, for example by dissolving a compound of the formula (I) in a suitable inert solvent and adding the acid, for example hydrochloric acid or nitric acid, and they can be isolated in a known manner, for example by filtering off and can, if appropriate, be purified by washing with or recrystallizing from a suitable inert organic solvent.

It is evident from the general formula (I) that the compounds according to the invention possess at least two asymmetric carbon atoms, which are located in the 2-position and 4-position of the dioxolane ring. These compounds can, accordingly, exist in the form of different stereoisomers.

The diastereomeric racemates (cis- or trans-form according to the rules described in C.A., Volume 76 (1972), Index Guide, Section IV, 203) of the compounds of the general formula (I) can be separated in a customary manner. Examples of suitable methods are selective crystallization and chromatography, for example column chromatography.

Since the stereochemical configuration is already present in the intermediate products of the general formula (II) or (V), the separation into the cis- and trans-forms can be carried out as early as this stage or, preferably, even earlier, for example at the stage of the intermediate products of the general formula (IV). The separation can be carried out easily by the methods described above. The cis- and trans-diastereomeric racemates can, in turn, be resolved in a customary manner into their optical antipodes cis(+) and cis(−) or trans(+) and trans(−), respectively.

The new compounds of the formula (I) are chemotherapeutic agents and possess an action, and a toleration, against fungal infections which is superior to that of the "Ketoconazol" mentioned at the outset. They have a very good action in vitro against skin fungi, such as, for example, *Trichophyton mentagrophytes, Microsporum canis* or *Epidermophytes floccosum;* mold fungi, such as, for example, *Aspergillus niger,* or yeasts, such as, for example, *Candida albicans, C.tropicalis, Torulpsis glabrata* and *Trichosporon cutaneum* or *Trichomonas vaginalis* or *T.fetus,* or Gram-positive and Gram-negative bacteria. In vivo too, for example in experimental renal candidiasis of mice, the compounds possess, when administered orally or parenterally, a very good systemic effect, for example against *Candida albicans.* When administered orally or parenterally or applied locally, there is also a very good effect against various pathogens of dermato mycoses (for example *Trichophyton mentagrophytes*) on guinea pigs.

Accordingly, the compounds of formula I according to the invention may be used to combat infections caused by fungi, protozoa or bacteria as mentioned above, by administering to the patient suffering from such infection an effective amount either locally, orally or parenterally in the form of a suitable pharmaceutical composition.

Examples of possible suitable composition containing a compound of formula I as the active ingredients are tablets or capsules, suspensions, solutions, jellies, creams or ointments and also aerosols in the form of spray.

The concentration of administration for solutions, jellies, creams or ointments and also aerosols in the form of spray is generally between 0.1 and 3 percent by weight. Oral administration is effected in formulations which are customary in pharmacy, for example in the form of tablets or capsules containing, per daily dose, 50–200 mg of the active compound mixed with a customary excipient and/or constituent. For local application, it is possible to use, for example, suspensions, solutions, jellies, creams, ointments or suppositories. Suitable suspensions or solutions in a concentration for administration of between 0.1 and 5 percent by weight are possible for parenteral administration.

The examples illustrate the invention.

EXAMPLES FOR THE FIRST PROCESS OF PREPARATION ACCORDING TO CLAIM 2

EXAMPLE 1

Cis-2-(2,4-dichlorophenyl)-2-(1H-imidazol-1-ylmethyl)-4-[4-chloro-2-(piperidin-1-ylmethyl)-phenoxymethyl]-1,3-dioxolane and its dinitrate.

(a) Preparation of the free compound 2.25 g=10 mmoles of 4-chloro-2-(piperidin-1-ylmethyl)-phenol are added in portions, while stirring and cooling by means of an ice bath, to a suspension of 0.3 g=10 mmoles of NaH (an 80% strength dispersion in oil) in 20 ml of absolute dimethylformamide, at such a rate that the temperature does not exceed 20° C., stirring is continued at 20° C. until the evolution of hydrogen is complete, 4.07 g=10 mmoles of cis-2-(2,4-dichlorophenyl)-2-(1H-imidazol-1-ylmethyl)-1,3-dioxolan-4-ylmethyl methanesulfonate are then introduced in portions and the mixture is heated at 80° C. for 8 hours. After cooling, the solvent is removed on a rotary evaporator under an oil pump vacuum, the residue is taken up in 100 ml of water, the solution is extracted with twice 30 ml of methylene chloride and the combined methylene chloride phases are rinsed with 30 ml of water, dried over sodium sulfate and evaporated in vacuo. The residue obtained (5.4 g) is purified by column chromatography over silica gel (silica gel S, Riedel-de Haën) using a 10:1 mixture of methylene chloride and ethanol as the migrating agent. The fractions shown to be homogeneous by a thin layer chromatogram (silica gel and 10:1 methylene chloride/ethanol) are combined and the solvent is removed. This gives 4.6 g (86% of theory) in the form of a highly viscous, non-crystalline oil.

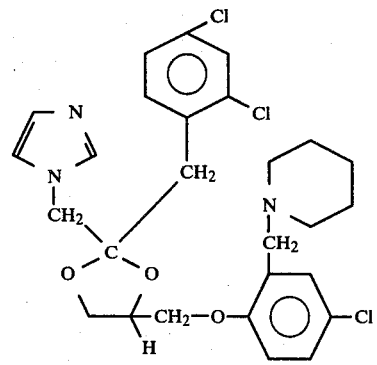

| | Analysis: Calculated: | Found: |
|---|---|---|
| $C_{26}H_{28}Cl_3N_3O_3$ | C: 58.17 | C: 57.5 |
| | H: 5.26 | H: 4.9 |
| | N: 7.83 | N: 7.6 |

Molecular weight: 536.86

Dimethyl sulfoxide, dimethylacetamide or N-methyl-2-pyrrolidone and also mixtures of these solvents with, for example, tetrahydrofuran, dioxane, dimethoxyethane or toluene, can also be used in the same procedure as that described above.

(b) Preparation of the dinitrate:

2 g=3.7 mmoles of the oil described above are dissolved in 60 ml of ethyl acetate and a solution of 0.31 ml=0.47 g=7.4 mmoles of 100% strength $HNO_3$ in 20 ml of ethyl acetate are added dropwise at 20° C., while stirring, the mixture is allowed to stand for 15 hours at 20° C., the solvent is removed in vacuo on a rotary evaporator and the residue is recrystallized from acetonitrile/ethyl acetate. This gives 1.2 g (49% of theory) of cis-2-(2,4-dichlorophenyl)-2-(1H-imidazol-1-ylmethyl)-4-[4-chloro-2-(piperidin-1-ylmethyl)-phenoxymethyl]-1,3-dioxolane in the form of the dinitrate. (Melting point: 140° C., decomposition).

| | Analysis: Calculated: | Found: |
|---|---|---|
| $C_{26}H_{30}Cl_3N_5O_9$ | C: 47.11 | C: 46.8 |
| | H: 4.56 | H: 4.7 |
| | N: 10.56 | N: 10.4 |

EXAMPLE 2

The following compounds of the general formula (I), listed in Table 1, can be prepared in accordance with Example 1, but using equivalent quantities of the corresponding compounds of the general formula (II) and (III).

TABLE 1

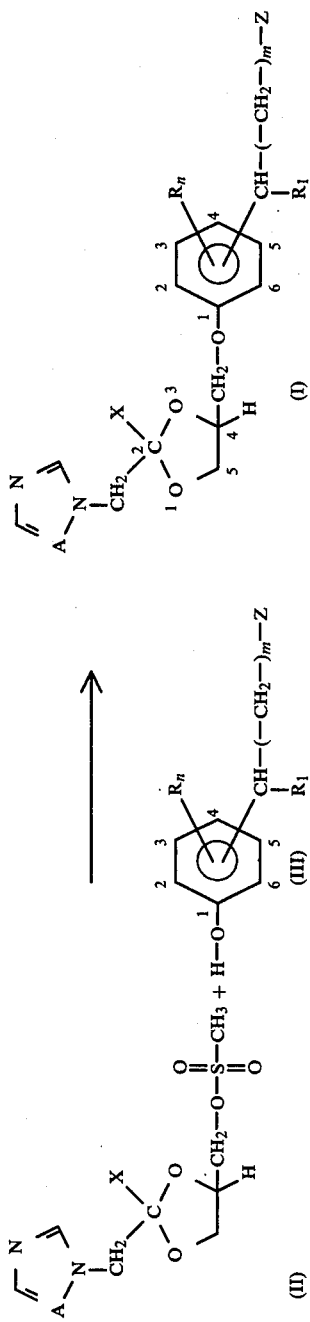

(a) in the Table, v indicates the position of the radical $-CH-(-CH_2-)_m-Z$ with $R_1$ underneath (b) Cis- and trans- relate to the azolylmethyl radical and the phenoxy radical in the 2-position and 4-position, respectively, of the dioxolane ring

| Compound No. | A | X | n | $R_n$ | (a) v | $R_1$ | m | Z | (b) 2,4-Isomer | Base or salt | Melting point: [°C] | Analysis Calculated: | | Found: |
|---|---|---|---|---|---|---|---|---|---|---|---|---|---|---|
| 1.1 | CH | 2,4-$Cl_2C_6H_3$ | 0 | | 2 | H | 0 | $-N(CH_3)_2$ | Cis | Base | | C: 59.78 H: 5.45 N: 9.08 | | C: 59.2 H: 5.4 N: 8.7 |
| 1.2 | CH | 2,4-$Cl_2C_6H_3$ | 0 | | 3 | H | 0 | $-N(CH_3)_2$ | Cis | Base | 74–76 | C: 59.75 H: 5.45 N: 9.09 | | C: 60.0 H: 5.2 N: 8.8 |
| 1.3 | CH | 2,4-$Cl_2C_6H_3$ | 0 | | 4 | H | 0 | $-N(CH_3)_2$ | Cis | Base | | C: 55.61 H: 4.87 N: 8.46 | | C: 55.3 H: 5.3 N: 8.2 |
| 1.4 | CH | 2,4-$Cl_2C_6H_3$ | 1 | 4-Cl | 2 | H | 0 | $-(CH_3)_2$ | Cis | Base | | | | |
| 1.5 | CH | 2,4-$Cl_2C_6H_3$ | 1 | 4-Cl | 2 | H | 0 | imidazole | Cis | Base | 124–126 | C: 55.45 H: 4.07 N: 10.77 | | C: 54.9 H: 4.2 N: 10.4 |
| 1.6 | CH | 2,4-$Cl_2C_6H_3$ | 1 | 4-Cl | 2 | H | 0 | pyrrolidine | Cis | Base | — | C: 57.40 H: 5.01 N: 8.04 | | C: 56.8 H: 5.0 N: 7.8 |
| 1.7 | CH | 2,4-$Cl_2C_6H_3$ | 1 | 4-Cl | 2 | H | 0 | piperidine | Cis | 2.$HNO_3$ | 140 | C: 47.11 H: 4.56 N: 10.56 | | C: 46.8 H: 4.7 N: 10.4 |

TABLE 1-continued

| No. | | Ar | | subst. | R | n | Z | | stereo | form | mp | Analysis calc. | found |
|---|---|---|---|---|---|---|---|---|---|---|---|---|---|
| 1.8 | CH | 2,4Cl₂C₆H₃ | | | H | 2 | morpholine | | Cis | Base | — | | C: 55.73 / H: 4.86 / N: 7.80 | C: 55.1 / H: 4.5 / N: 7.6 |
| 1.9 | CH | 2,4Cl₂C₆H₃ | 1 | 4-Cl | H | 2 | pyrazolyl | | Cis | Base | 107 | C: 55.46 / H: 4.07 / N: 10.78 | C: 55.9 / H: 4.4 / N: 11.1 |
| 1.10 | CH | 2,4Cl₂C₆H₃ | 1 | 4-Br | H | 2 | O | —N(CH₃)₂ | Cis | Base | | | |
| 1.11 | CH | 2,4Cl₂C₆H₃ | 1 | 4-F | H | 2 | O | —N(CH₃)₂ | Cis | Base | | | |
| 1.12 | CH | 2,4Cl₂C₆H₃ | 1 | 4-CF₃ | H | 2 | O | —N(CH₃)₂ | Cis | Base | | | |
| 1.13 | CH | 2,4Cl₂C₆H₃ | 1 | 4-CH₃ | H | 2 | O | —(CH₃)₂ | Cis | Base | | | |
| 1.14 | CH | 2,4Cl₂C₆H₃ | 1 | 4-tert-butyl | H | 2 | O | —N(CH₃)₂ | Cis | Base | | | |
| 1.15 | CH | 2,4Cl₂C₆H₃ | 1 | 4-tert-butyl | H | 2 | imidazolyl | | Cis | Base | 149–150 | C: 62.16 / H: 5.59 / N: 10.25 | C: 62.0 / H: 5.8 / N: 10.3 |
| 1.16 | CH | 2,4Cl₂C₆H₃ | 1 | 4-tert-butyl | H | 2 | imidazolyl | | Cis | Dinitrate | 230 | C: 50.38 / H: 4.83 / N: 12.60 | C: 50.4 / H: 4.9 / N: 12.4 |
| 1.17 | CH | 2,4Cl₂C₆H₃ | 1 | 4-CH₃—C(CH₃)₂—CH₂—C(CH₃)— | H | 2 | imidazolyl | | Cis | Base | | | |
| 1.18 | CH | 2,4Cl₂C₆H₃ | 1 | 4-CH₃—C(CH₃)₂—CH₂—C(CH₃)— | H | 2 | O | —N(CH₃)₂ | Cis | Base | 147 | C: 64.27 / H: 6.40 / N: 9.37 | C: 63.9 / H: 6.4 / N: 9.3 |
| 1.19 | CH | 2,4Cl₂C₆H₃ | 1 | 4-O—CH₃ | H | 2 | O | —N(CH₃)₂ | Cis | Base | 114 | C: 58.26 / H: 4.69 / N: 10.87 | C: 57.8 / H: 5.0 / N: 10.5 |
| 1.20 | CH | 2,4Cl₂C₆H₃ | 1 | 4-O—CH₃ | H | 2 | O | —N(CH₃)₂ | Cis | Base | | | |
| 1.21 | CH | 2,4Cl₂C₆H₃ | 1 | 4-O—C₄H₉ | H | 2 | O | —N(CH₃)₂ | Cis | Base | | | |
| 1.22 | CH | 2,4Cl₂C₆H₃ | 3 | 2,4,5 Cl₃ | H | 6 | O | —N(CH₃)₂ | Cis | Base | | | |

TABLE 1-continued

| No. | | | | | | | | | Analysis calc. | Analysis found |
|---|---|---|---|---|---|---|---|---|---|---|
| 1.23 | CH | 2,4Cl$_2$C$_6$H$_3$ | 1 | $-\overset{\overset{\displaystyle O}{\|}}{C}-O-C_2H_5$ | 2 | H | 0 | Cis | Base | — | C: 58.18<br>H: 4.70<br>N: 10.05 | C: 58.2<br>H: 5.0<br>N: 9.7 |
| 1.24 | CH | 2,4Cl$_2$C$_6$H$_3$ | 1 | $-\overset{\overset{\displaystyle O}{\|}}{C}-O-CH_3$ | 2 | H | 0 | Cis | Base | — | C: 56.76<br>H: 4.19<br>N: 10.59 | C: 56.5<br>H: 4.0<br>N: 10.2 |
| 1.25 | CH | 2,4Cl$_2$C$_6$H$_3$ | 1 | $-\overset{\overset{\displaystyle O}{\|}}{C}-OH$ | 2 | H | 0 | Cis | Base | — | C: 59.80<br>H: 6.19<br>N: 11.62 | C: 59.5<br>H: 6.0<br>N: 11.1 |
| 1.26 | CH | 2,4Cl$_2$C$_6$H$_3$ | 1 | 2-CH$_2$—N(CH$_3$)$_2$ | 4 | H | 0 | Cis | Base | — | | |
| 1.27 | CH | 2,4Cl$_2$C$_6$H$_3$ | 1 | 4-NO$_2$ | 2 | H | 0 | Cis | Base | 143-144 | C: 62.81<br>H: 4.51<br>N: 10.46 | C: 62.7<br>H: 4.6<br>N: 10.4 |
| 1.28 | CH | 2,4Cl$_2$C$_6$H$_3$ | 2 | 3,4-C$_4$H$_4$ | 2 | H | 0 | Cis | Base | — | C: 63.28<br>H: 5.31<br>N: 8.20 | C: 63.1<br>H: 5.2<br>N: 8.0 |
| 1.29 | CH | 2,4Cl$_2$C$_6$H$_3$ | 2 | 3,4-C$_4$H$_4$ | 2 | H | 0 | Cis | Base | | | |
| 1.30 | CH | 2,4Cl$_2$C$_6$H$_3$ | 2 | 3,4-C$_4$H$_4$ | 2 | C$_6$H$_5$ (phenyl) | 0 | Cis | Base | | | |
| 1.31 | CH | 2,4Cl$_2$C$_6$H$_3$ | 2 | 3,4-C$_4$H$_4$ | 2 | 4-NO$_2$-C$_6$H$_4$ | 0 | Cis | Base | | | |
| 1.32 | CH | 2,4Cl$_2$C$_6$H$_3$ | 2 | 3,4-C$_4$H$_4$ | 2 | 4-Cl-C$_6$H$_4$ | 0 | Cis | Base | 75-80 | C: 63.62<br>H: 4.85<br>N: 6.75 | C: 63.7<br>H: 5.1<br>N: 6.8 |

TABLE 1-continued

| No. | | | | | | | | | | | Analysis |
|---|---|---|---|---|---|---|---|---|---|---|---|
| 1.33 | CH | 2,4Cl₂C₆H₃ | 2 | 3,4-C₄H₄ | 2 | 4-CF₃-C₆H₄ | 0 | —N(CH₃)₂ | Cis | Base | |
| 1.34 | N | 2,4Cl₂C₆H₃ | 2 | 3,4-C₄H₄ | 2 | H | 0 | —N(CH₃)₂ | Cis | Base | |
| 1.35 | N | 2,4Cl₂C₆H₃ | 2 | 3,4-C₄H₄ | 2 | 4-Cl-C₆H₄ | 0 | —N(CH₃)₂ | Cis | Base | |
| 1.36 | CH | 2,4Cl₂C₆H₃ | 1 | 4-O-(4-Cl-C₆H₄) | 2 | H | 0 | —N(CH₃)₂ | Cis | Base | |
| 1.37 | CH | 2,4Cl₂C₆H₃ | 1 | 4-O-(2,4-Cl₂-C₆H₃) | 2 | H | 0 | —N(CH₃)₂ | Cis | Base | |
| 1.38 | CH | 2,4Cl₂C₆H₃ | 1 | 4-O-(2,4-Cl₂-C₆H₃) | 2 | H | 0 | imidazolyl | Cis | Base | C: 55.75 C: 55.9<br>H: 3.74 H: 4.0<br>N: 8.67 N: 8.7 |
| 1.39 | CH | 2,4Cl₂C₆H₃ | 1 | 4-O-(4-OCH₃-C₆H₄) | 2 | H | 0 | —N(CH₃)₂ | Cis | Base | — |
| 1.40 | CH | 2,4Cl₂C₆H₃ | 1 | 4-O-(4-CF₃-C₆H₄) | 2 | H | 0 | —N(CH₃)₂ | Cis | Base | |
| 1.41 | CH | 2,4Cl₂C₆H₃ | 1 | 4-O-(4-CH₃-C₆H₄) | 2 | H | 0 | —N(CH₃)₂ | Cis | Base | |

TABLE 1-continued

| | | | | | | | | |
|---|---|---|---|---|---|---|---|---|
| 1.42 | CH | 2,4Cl$_2$C$_6$H$_3$ | 2 | 4,6-Cl$_2$ | H | 0 |  | Cis | Base | — | C: 53.26 C: 52.9<br>H: 4.81 H: 4.8<br>N: 9.56 N: 9.3 |
| 1.43 | CH | 2,4Cl$_2$C$_6$H$_3$ | 2 | 4,6-Cl$_2$ | H | 0 |  | Cis | Base | — | C: 52.03 C: 51.7<br>H: 3.64 H: 3.8<br>N: 10.11 N: 9.8 |
| 1.44 | CH | 2,4Cl$_2$C$_6$H$_3$ | 2 | 4,6-Cl$_2$ | H | 0 |  | Cis | Base | — | C: 49.77 C: 50.0<br>H: 3.45 H: 3.6<br>N: 12.62 N: 12.3 |
| 1.45 | CH | 2,4Cl$_2$C$_6$H$_3$ | 2 | 2,6-diiso-propyl | H | 0 |  | Cis | Base | — | C: 61.06 C: 61.0<br>H: 5.83 H: 5.9<br>N: 12.28 N: 12.1 |
| 1.46 | CH | 2,4Cl$_2$C$_6$H$_3$ | 2 | 2,6-diiso-propyl | H | 0 | —N(CH$_3$)$_2$ | Cis | Base | | C: 63.74 C: 63.5<br>H: 6.82 H: 6.8<br>N: 7.69 N: 7.5 |
| 1.47 | CH | 2,4Cl$_2$C$_6$H$_3$ | 2 | 2-CH$_3$<br>6-CH$_2$—CH—CH$_2$ | H | 0 | —N(CH$_3$)$_2$ | Cis | Base | | |
| 1.48 | CH | 2,4Cl$_2$C$_6$H$_3$ | 2 | 2-Cl<br>6-CH$_2$—CH—CH$_2$ | H | 0 | —N(CH$_3$)$_2$ | Cis | Base | | |
| 1.49<br>1.50 | CH<br>CH | 2,4Cl$_2$C$_6$H$_3$<br>2,4Cl$_2$C$_6$H$_3$ | 2<br>2 | 2,6-diethyl<br>2,6-ditert.-butyl | H<br>H | 0<br>0 | —N(CH$_3$)$_2$<br>—N(CH$_3$)$_2$ | Cis<br>Cis | Base<br>Base | | |
| 1.51 | CH | 2,4Cl$_2$C$_6$H$_3$ | 0 | | —C$_4$H$_9$ | 0 |  | Cis | Base | | |
| 1.52<br>1.53 | CH<br>CH | 2,4Cl$_2$C$_6$H$_3$<br>2,4Cl$_2$C$_6$H$_3$ | 0<br>2 | 2,6-di-tert.-butyl | —C$_3$H$_7$<br>H | 0<br>0 | —N(C$_2$H$_5$)$_2$<br>—N(C$_2$H$_5$)$_2$ | Cis<br>Cis | Base<br>Base | | |
| 1.54 | CH | 2,4Cl$_2$C$_6$H$_3$ | 2 | 2,6-diiso-propyl | H | 0 | —N(C$_2$H$_5$)$_2$ | Cis | Base | | |
| 1.55 | CH | 2,4Cl$_2$C$_6$H$_3$ | 2 | 2,6-di-methoxy | H | 0 | —N(CH$_3$)$_2$ | Cis | Base | | |
| 1.56 | CH | 2,4Cl$_2$C$_6$H$_3$ | 2 | 2,6-di-methoxy | H | 0 | —N(C$_2$H$_5$)$_2$ | Cis | Base | | |

TABLE 1-continued

| No. | | | | | | | | | |
|---|---|---|---|---|---|---|---|---|---|
| 1.57 | CH | 2,4Cl₂C₆H₃ | 2 | 2,6-dimethoxy | 4 | H | 0 |  | Cis Base |
| 1.58 | CH | 2,4Cl₂C₆H₃ | 2 | 2,6-diethyl | 4 | H | 0 | —N(C₂H₅)₂ | Cis Base |
| 1.59 | N | 2,4Cl₂C₆H₃ | 2 | 2,6-diethyl | 4 | H | 0 | —N(CH₃)₂ | Cis Base |
| 1.60 | N | 2,4Cl₂C₆H₃ | 2 | 2,6-diisopropyl | 4 | H | 0 | —N(CH₃)₂ | Cis Base |
| 1.61 | N | 2,4Cl₂C₆H₃ | 2 | 2,6-di-tert.-butyl | 4 | H | 0 | —N(CH₃)₂ | Cis Base |
| 1.62 | CH | 4-ClC₆H₄ | 2 | 2,6-diethyl | 4 | H | 0 | —N(C₂H₅)₂ | Cis Base |
| 1.63 | CH | 4-ClC₆H₄ | 2 | 2,6-diisopropyl | 4 | H | 0 | —N(C₂H₅)₂ | Cis Base |
| 1.64 | CH | 2,4-C₆H₃ | 2 | 2,6-diethyl | 4 | H | 0 |  | Cis Base |
| 1.65 | CH | 2,4-C₆H₃ | 2 | 2,6-diisopropyl | 4 | H | 0 | 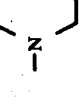 | Cis Base |
| 1.66 | CH | 2,4-C₆H₃ | 2 | 2,6-diethyl | 4 | H | 0 |  | Cis Base |
| 1.67 | CH | 2,4-C₆H₃ | 2 | 2,6-diisopropyl | 4 | H | 0 |  | Cis Base |
| 1.68 | CH | 2,4-C₆H₃ | 2 | 2,6-dimethoxy | 4 | H | 0 | 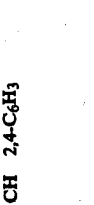 | Cis Base |
| 1.69 | CH | 2,4-Cl₂C₆H₃ | 2 | 2,6-dibromo | 4 | H | 0 | —N(CH₃)₂ | Cis Base |
| 1.70 | CH | 2,4-Cl₂C₆H₃ | 2 | 2,6-dibromo | 4 | H | 0 | —N(C₂H₅)₃ | Cis Base |

TABLE 1-continued

| No. | | | | | | | | | Stereo | Salt | Analysis |
|---|---|---|---|---|---|---|---|---|---|---|---|
| 1.71 | CH | 2,4-Cl$_2$C$_6$H$_3$ | 2 | 2,6-dibromo | 4 | H | | ![pyrrolidinyl] −N⟨⟩ (pyrrolidine) | Cis | Base | — |
| 1.72 | CH | 2,4-Cl$_2$C$_6$H$_3$ | 2 | 2,6-dibromo | 4 | H | 0 | −N(−CH$_2$−CH−CH$_2$)$_2$ | Cis | Base | C: 61.23 C: 60.8<br>H: 5.96 H: 6.3<br>N: 8.57 N: 8.7 |
| 1.73 | CH | 2,4-Cl$_2$C$_6$H$_3$ | 2 | 2,6-dimethyl | 4 | H | 0 | −N(CH$_3$)$_2$ | Cis | Base | C: 62.54 C: 62.0<br>H: 6.41 H: 6.4<br>N: 8.10 N: 7.8 |
| 1.74 | CH | 2,4-Cl$_2$C$_6$H$_3$ | 2 | 2,6-dimethyl | 4 | H | 0 | −N(C$_2$H$_5$)$_2$ | Cis | Base | — |
| 1.75 | CH | 2,4-Cl$_2$C$_6$H$_3$ | 2 | 2,6-dimethyl | 4 | H | 0 | −N(C$_4$H$_9$)$_2$ | Cis | Base | — |
| 1.76 | CH | 2,4-Cl$_2$C$_6$H$_3$ | 2 | 2,6-dimethyl | 4 | H | 0 | −N(−CH$_2$−CH−CH$_2$)$_2$ | Cis | Base | C: 64.32 C: 64.3<br>H: 5.96 H: 6.2<br>N: 7.76 N: 7.6 |
| 1.77 | CH | 2,4-Cl$_2$C$_6$H$_3$ | 2 | 2,6-dimethyl | 4 | H | 0 | −NH−C$_4$H$_9$ | Cis | Base | |
| 1.78 | CH | 2,4-Cl$_2$C$_6$H$_3$ | 2 | 2,6-dimethyl | 4 | H | 0 | −NH−C$_8$H$_{17}$ | Cis | Base | |
| 1.79 | CH | 2,4-Cl$_2$C$_6$H$_3$ | 2 | 2,6-dimethyl | 4 | H | 0 | CH$_3$<br>\|<br>−N−C$_4$H$_9$ | Cis | Base | |
| 1.80 | CH | 2,4-Cl$_2$C$_6$H$_3$ | 2 | 2,6-dimethyl | 4 | H$_3$C | 0 | CH$_3$<br>\|<br>Ph−C−H<br>\|<br>NH− | Cis | Base | |
| 1.81 | CH | 2,4-Cl$_2$C$_6$H$_3$ | 2 | 2,6-dimethyl | 4 | H | 0 | −N(CH$_3$)$_2$ | Cis | Base | |
| 1.82 | CH | 2,4-Cl$_2$C$_6$H$_3$ | 2 | 2,6-dimethyl | 4 | H | 0 | −N(C$_3$H$_7$)$_2$ | Cis | Base | |
| 1.83 | CH | 2,4-Cl$_2$C$_6$H$_3$ | 2 | 2,6-dimethyl | 4 | H | 0 | −N[−CH(CH$_3$)$_2$]$_2$ | Cis | Base | |
| 1.84 | CH | 2,4-Cl$_2$C$_6$H$_3$ | 2 | 2,6-dimethyl | 4 | H | 0 | −NH−tert.-butyl | Cis | Base | |
| 1.85 | CH | 2,4-Cl$_2$C$_6$H$_3$ | 2 | 2,6-dimethyl | 4 | H | 0 | CH$_3$<br>\|<br>−N−CH$_2$−CH−CH$_2$ | Cis | Base | |
| 1.86 | CH | 2,4-Cl$_2$C$_6$H$_3$ | 2 | 2,6-dimethyl | 4 | H | 0 | −N(−CH$_2$−C$_6$H$_5$)$_2$ | Cis | Base | |

TABLE 1-continued
| | | | | | | | | |
|---|---|---|---|---|---|---|---|---|
| 1.87 | CH | 2,4-Cl₂C₆H₃ | 2 | 2,6-di-methyl | H |  | Cis | Base | |
| 1.88 | CH | 2,4-Cl₂C₆H₃ | 2 | 2,6-di-methyl | H |  | Cis | Base | |
| 1.89 | CH | 2,4-Cl₂C₆H₃ | 2 | 2,6-di-methyl | H |  | Cis | .2HNO₃ | 159 | C: 49.83  49.6<br>H: 4.33  4.3<br>N: 10.02  10.0 |
| 1.90 | CH | 2,4-Cl₂C₆H₃ | 2 | 2,6-di-methyl | H |  | Cis | Base | |
| 1.91 | CH | 2,4-Cl₂C₆H₃ | 2 | 2,6-di-methyl | H | | Cis | Base | |
| 1.92 | CH | 2,4-Cl₂C₆H₃ | 2 | 2,6-di-methyl | H | | Cis | Base | |
| 1.93 | CH | 2,4-Cl₂C₆H₃ | 2 | 2,6-di-methyl | H |  | Cis | Base | |
| 1.94 | CH | 2,4-Cl₂C₆H₃ | 2 | 2,6-di-methyl | H |  | Cis | Base | |
| 1.95 | CH | 2,4-Cl₂C₆H₃ | 2 | 2,6-di-methyl | H |  | Cis | Base | — | C: 60.74  60.2<br>H: 5.98  6.2<br>N: 9.77  9.8 |

TABLE 1-continued

| | | | | | | | | |
|---|---|---|---|---|---|---|---|---|
| 1.96 | CH | 2,4-Cl$_2$C$_6$H$_3$ | 2 | 2,6-di-methyl | H | 4 | 0 | piperazine N—CH$_2$—C(=O)—CH$_3$ | Cis | Base | C: 55.17 C: 54.7<br>H: 5.62 H: 5.8<br>N: 9.19 N: 9.3 |
| 1.97 | CH | 2,4-Cl$_2$C$_6$H$_3$ | 2 | 2,6-di-methyl | H | 4 | 0 | piperazine N—CH$_2$—C(=O)—C(CH$_3$)$_3$ | Cis | Base | — |
| 1.98 | CH | 2,4-Cl$_2$C$_6$H$_3$ | 2 | 2,6-di-methyl | H | 4 | 0 | piperazine N—SO$_2$—CH$_3$ | Cis | Base | C: 65.23 C: 64.9<br>H: 5.97 H: 6.2<br>N: 9.22 N: 9.1 |
| 1.99 | CH | 2,4-Cl$_2$C$_6$H$_3$ | 2 | 2,6-di-methyl | H | 4 | 0 | piperazine N—C$_6$H$_5$ | Cis | Base | C: 61.74 C: 61.0<br>H: 5.50 H: 5.5<br>N: 8.73 N: 8.6 |
| 1.100 | CH | 2,4-Cl$_2$C$_6$H$_3$ | 2 | 2,6-di-methyl | H | 4 | 0 | piperazine N—(4-Cl-C$_6$H$_4$) | Cis | Base | — |
| 1.101 | CH | 2,4-Cl$_2$C$_6$H$_3$ | 2 | 2,6-di-methyl | H | 4 | 0 | piperazine N—CH$_2$—C$_6$H$_5$ | Cis | Base | |
| 1.102 | CH | 2,4-Cl$_2$C$_6$H$_3$ | 2 | 2,6-di-methyl | H | 4 | 0 | piperazine N—CH$_2$—(4-Cl-C$_6$H$_4$) | Cis | Base | C: 62.25 C: 61.9<br>H: 5.68 H: 5.6<br>N: 8.54 N: 8.4 |
| 1.103 | CH | 2,4-Cl$_2$C$_6$H$_3$ | 2 | 2,6-di-methyl | H | 4 | 0 | piperazine N—CH$_2$—(2,4-Cl$_2$-C$_6$H$_3$) | Cis | Base | |

TABLE 1-continued

| | | | | | | | | | |
|---|---|---|---|---|---|---|---|---|---|
| 1.104 | CH | 2,4-Cl$_2$C$_6$H$_3$ | 2 | 2,4-di-methyl | 4 | H | O |  N—CH$_2$—C$_6$H$_4$—CF$_3$ | Cis Base | — |
| 1.105 | CH | 2,4-Cl$_2$C$_6$H$_3$ | 2 | 2,6-di-methyl | 4 | H | O | N—CH$_2$—C$_6$H$_4$—CH$_3$ | Cis Base | — |
| 1.106 | CH | 2,4-Cl$_2$C$_6$H$_3$ | 2 | 2,6-di-methyl | 4 | H | O | N—CH$_2$—C$_6$H$_4$—OCH$_3$ | Cis Base | — |
| 1.107 | CH | 2,4-Cl$_2$C$_6$H$_3$ | 2 | 2,6-di-methyl | 4 | H | O | N—C$_6$H$_4$—CF$_3$ | Cis Base | — |
| 1.108 | CH | 2,4-Cl$_2$C$_6$H$_3$ | 2 | 2,6-di-methyl | 4 | H | O | N—C$_6$H$_4$—CH$_3$ | Cis Base | — |
| 1.109 | CH | 2,4-Cl$_2$C$_6$H$_3$ | 2 | 2,6-di-methyl | 4 | H | O | N—C$_6$H$_4$—OCH$_3$ | Cis Base | C: 64.05 63.6<br>H: 6.01 6.1<br>N: 8.79 8.4 |
| 1.110 | CH | 2,4-Cl$_2$C$_6$H$_3$ | 2 | 2,6-di-methyl | 4 | H | O |  (imidazolyl) | Cis Base | — |
| 1.111 | CH | 2,4-Cl$_2$C$_6$H$_3$ | 2 | 2,6-di-methyl | 4 | H | O |  (pyrrolidinyl) | Cis Base | C: 62.79 62.2<br>H: 6.05 6.2<br>N: 8.14 7.8 |

TABLE 1-continued

| | | | | | | | | |
|---|---|---|---|---|---|---|---|---|
| 1.112 | CH | 2,4-Cl$_2$C$_6$H$_3$ | 2 | 2,6-di-methyl | 4 | H | 0 |  | Cis | Base | — | C: 63.39 63.1<br>H: 6.27 6.3<br>N: 7.92 7.6 |
| 1.113 | CH | 2,4-Cl$_2$C$_6$H$_3$ | 2 | 2,6-di-methyl | 4 | H | 0 |  | Cis | Base | — | C: 60.90 60.2<br>H: 5.87 5.8<br>N: 7.89 7.5 |
| 1.114 | CH | 2,4-Cl$_2$C$_6$H$_3$ | 2 | 2,6-di-methyl | 4 | H | 0 |  | Cis | Base | — | C: 59.12 58.6<br>H: 5.70 6.1<br>N: 5.11 4.7 |
| 1.115 | CH | 2,4-Cl$_2$C$_6$H$_3$ | 2 | 2,6-di-methyl | 4 | H | 0 |  | Cis | Base | — | |
| 1.116 | CH | 2,4-Cl$_2$C$_6$H$_3$ | 2 | 2,6-di-methyl | 4 | H | 0 | 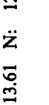 | Cis | Base | — | |
| 1.117 | CH | 2,4-Cl$_2$C$_6$H$_3$ | 2 | 2,6-di-methyl | 4 | H | 0 |  | Cis | Base | — | C: 58.37 57.5<br>H: 4.90 4.6<br>N: 13.61 12.9 |
| 1.118 | N | 2,4-Cl$_2$C$_6$H$_3$ | 2 | 2,6-di-methyl | 4 | H | 0 | —N(C$_2$H$_5$)$_2$ | Cis | Base | | |
| 1.119 | N | 2,4-Cl$_2$C$_6$H$_3$ | 2 | 2,6-di-methyl | 4 | H | 0 |  | Cis | Base | | |
| 1.120 | N | 2,4-Cl$_2$C$_6$H$_3$ | 2 | 2,6-di-methyl | 4 | H | 0 |  | Cis | Base | | |

TABLE 1-continued

| | | | | | | | | | |
|---|---|---|---|---|---|---|---|---|---|
| 1.121 | N | 4-BrC$_6$H$_4$ | 2 | 2,6-di-methyl | H | O | —N(C$_2$H$_5$)$_2$ | | Base |
| 1.122 | CH | 4-CH$_3$—C$_6$H$_4$ | 2 | 2,6-di-methyl | H | O | —N(C$_2$H$_5$)$_2$ | | Base |
| 1.123 | N | 2,4-Cl$_2$C$_6$H$_3$ | 2 | 2,6-di-methyl | H | O | 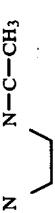 | Cis | Base |
| 1.124 | CH |  | 2 | 2,6-di-methyl | H | O | —N(C$_2$H$_5$)$_2$ | | Base |
| 1.125 | CH |  | 2 | 2,6-di-methyl | H | O | —N(C$_2$H$_5$)$_2$ | | Base |
| 1.126 | CH | 2,4-Cl$_2$C$_6$H$_3$ | 2 | 2-Cl; 6-CH$_3$ | H | O | —N(C$_2$H$_5$)$_2$ | Cis | Base |
| 1.127 | CH | 2,4-Cl$_2$C$_6$H$_3$ | 2 | 2-Cl; 6-CH$_3$ | H | O | —N(C$_4$H$_9$)$_2$ | Cis | Base |
| 1.128 | CH | 2,4-Cl$_2$C$_6$H$_3$ | 2 | 2-Cl; 6-CH$_3$ | H | O | —N(—CH$_2$—CH—CH$_2$)$_2$ | Cis | Base |
| 1.129 | CH | 2,4-Cl$_2$C$_6$H$_3$ | 2 | 2-Cl; 6-CH$_3$ | H | O | —N(C$_3$H$_7$)$_2$ | Cis | Base |
| 1.130 | CH | 2,4-Cl$_2$C$_6$H$_3$ | 2 | 2-Cl; 6-CH$_3$ | H | O | —N[—CH(CH$_3$)$_2$]$_2$ | Cis | Base |
| 1.131 | CH | 2,4-Cl$_2$C$_6$H$_3$ | 2 | 2-Cl; 6-CH$_3$ | H | O | $\overset{CH_3}{-N-CH_2-CH-CH_2}$ | Cis | Base |
| 1.132 | CH | 2,4-Cl$_2$C$_6$H$_3$ | 2 | 2-Cl; 6-CH$_3$ | H | O |  | Cis | Base | C: 57.30 C: 57.3<br>H: 5.52 H: 5.3<br>N: 9.90 N: 9.2 |
| 1.133 | CH | 2,4-Cl$_2$C$_6$H$_3$ | 2 | 2-Cl; 6-CH$_3$ | H | O |  | Cis | Base |

TABLE 1-continued
| | | | | | | | | |
|---|---|---|---|---|---|---|---|---|
| 1.134 | CH | 2,4-Cl$_2$C$_6$H$_3$ | 2 | 2-Cl; 6-CH$_3$ | 4 | H | 0 |  | Cis | Base | — |
| 1.135 | CH | 2,4-Cl$_2$C$_6$H$_3$ | 2 | 2-Cl; 6-CH$_3$ | 4 | H | 0 |  | Cis | Base | C: 56.63 C: 55.9<br>H: 5.26 H: 5.1<br>N: 9.43 N: 9.0 |
| 1.136 | CH | 2,4-Cl$_2$C$_6$H$_3$ | 2 | 2-Cl; 6-CH$_3$ | 4 | H | 0 |  | Cis | Base | — |
| 1.137 | CH | 2,4-Cl$_2$C$_6$H$_3$ | 2 | 2-Cl; 6-CH$_3$ | 4 | H | 0 |  | Cis | Base | — |
| 1.138 | CH | 2,4-Cl$_2$C$_6$H$_3$ | 2 | 2-Cl; 6-CH$_3$ | 4 | H | 0 |  | Cis | Base | — |
| 1.139 | CH | 2,4-Cl$_2$C$_6$H$_3$ | 2 | 2-Cl; 6-CH$_3$ | 4 | H | 0 |  | Cis | Base | — |
| 1.140 | CH | 2,4-Cl$_2$C$_6$H$_3$ | 2 | 2-Cl; 6-CH$_3$ | 4 | H | 0 | | Cis | Base | C: 56.25 C: 55.9<br>H: 4.34 H: 4.1<br>N: 10.50 N: 10.1 |
| 1.141 | CH | 2,4-Cl$_2$C$_6$H$_3$ | 2 | 2-Cl; 6-CH$_3$ | 4 | H | 0 | | Cis | Base | |

TABLE 1-continued

| No. | | | | | | | | | | | Elemental Analysis |
|---|---|---|---|---|---|---|---|---|---|---|---|
| 1.142 | CH | 2,4-Cl₂C₆H₃ | 2 | 2-Cl; 6-CH₃ | 4 | H | 0 | —N(piperidine) | Cis | Base | — |
| 1.143 | CH | 2,4-Cl₂C₆H₃ | 2 | 2-Cl; 6-CH₃ | 4 | H | 0 | —N(morpholine) | Cis | Base | C: 56.48  57.1<br>H: 5.1  5.2<br>N: 7.6  7.7 |
| 1.144 | CH | 2,4-Cl₂C₆H₃ | 2 | 2-Cl; 6-CH₃ | 4 | H | 0 | —N(thiomorpholine) | Cis | Base | C: 54.89  54.5<br>H: 4.96  5.2<br>N: 7.38  7.5 |
| 1.145 | CH | 2,4-Cl₂C₆H₃ | 2 | 2-Cl; 6-CH₃ | 4 | H | 0 | —N(tetrahydroisoquinoline) | Cis | Base | C: 62.17  61.8<br>H: 5.05  5.0<br>N: 7.01  6.9 |
| 1.146 | N | 2,4-Cl₂C₆H₃ | 2 | 2-Cl; 6-CH₃ | 4 | H | 0 | —N(CH₃)₂ | Cis | Base | C: 57.87  57.7<br>H: 5.49  5.6<br>N: 11.74  11.9 |
| 1.147 | CH | 4-Cl—C₆H₄ | 2 | 2-Cl; 6-CH₃ | 4 | H | 0 | —N(CH₃)₂ | | Base | C: 60.56  60.6<br>H: 5.71  5.7<br>N: 8.82  8.9 |
| 1.148 | CH | 2,4-Cl₂C₆H₃ | 2 | 2,6-dichloro | 4 | H | 0 | —N(CH₃)₂ | Cis | Base | C: 53.06  52.5<br>H: 4.27  4.6<br>N: 7.73  7.5 |
| 1.149 | CH | 2,4-Cl₂C₆H₃ | 2 | 2,6-dichloro | 4 | H | 0 | —N(C₂H₅)₂ | Cis | Base | — |
| 1.150 | CH | 2,4-Cl₂C₆H₃ | 2 | 2,6-dichloro | 4 | H | 0 | —N(—CH₂—CH—CH₂)₂ | Cis | Base | — |
| 1.151 | CH | 2,4-Cl₂C₆H₃ | 2 | 2,6-dichloro | 4 | H | 0 | —N(CH₃)—N—C₄H₉ | Cis | Base | — |
| 1.152 | CH | 2,4-Cl₂C₆H₃ | 2 | 2,6-dichloro | 4 | H | 0 | —N(piperazine)N—CH₃ | Cis | Base | — |
| 1.153 | CH | 2,4-Cl₂C₆H₃ | 2 | 2,6-dichloro | 4 | H | 0 | —N(piperazine)N—C₂H₅ | Cis | Base | — |

TABLE 1-continued
| | | | | | | | | |
|---|---|---|---|---|---|---|---|---|
| 1.154 | CH | 2,4-Cl$_2$C$_6$H$_3$ | 2 | 2,6-dichloro | 4 | H | 0 |  | Cis | Base |
| 1.155 | CH | 2,4-Cl$_2$C$_6$H$_3$ | 2 | 2,6-dichloro | 4 | H | 0 |  | Cis | Base |
| 1.156 | CH | 2,4-Cl$_2$C$_6$H$_3$ | 2 | 2,6-dichloro | 4 | H | 0 |  | Cis | Base | C: 52.78 C: 52.7<br>H: 4.59 H: 4.6<br>N: 9.12 N: 9.0 |
| 1.157 | CH | 2,4-Cl$_2$C$_6$H$_3$ | 2 | 2,6-dichloro | 4 | H | 0 |  | Cis | Base |
| 1.158 | CH | 2,4-Cl$_2$C$_6$H$_3$ | 2 | 2,6-dichloro | 4 | H | 0 |  | Cis | Base |
| 1.159 | CH | 2,4-Cl$_2$C$_6$H$_3$ | 2 | 2,6-dichloro | 4 | H | 0 |  | Cis | Base |
| 1.160 | CH | 2,4-Cl$_2$C$_6$H$_3$ | 2 | 2,6-dichloro | 4 | H | 0 |  | Cis | Base |
| 1.161 | CH | 2,4-Cl$_2$C$_6$H$_3$ | 2 | 2,6-dichloro | 4 | H | 0 |  | Cis | Base |
| 1.162 | CH | 2,4-Cl$_2$C$_6$H$_3$ | 2 | 2,6-dichloro | 4 | H | 0 |  | Cis | Base |

TABLE 1-continued

| | | | | | | | | |
|---|---|---|---|---|---|---|---|---|
| 1.163 | CH | 2,4-Cl$_2$C$_6$H$_3$ | 2 | 2,6-dichloro | H | 0 | 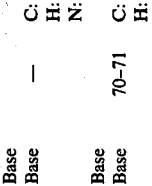 | Cis | Base | — | |
| 1.164 | CH | 4-Br—C$_6$H$_5$ | 2 | 2,6-dichloro | H | 0 | —N(C$_2$H$_5$)$_2$ | | Base | | |
| 1.165 | CH | 4-Cl—C$_6$H$_5$ | 2 | 2,6-dichloro | H | 0 | 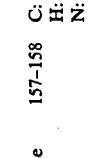 | | Base | | |
| 1.166 | CH | 2,4-Cl$_2$C$_6$H$_3$ | 0 | | H | 0 | —N(CH$_3$)$_2$ | Cis | Base | — | C: 59.75  C: 59.3<br>H: 5.45  H: 5.1<br>N: 9.10  N: 9.3 |
| 1.167 | CH | 2,4-Cl$_2$C$_6$H$_3$ | 0 | | H | 0 | —N(C$_2$H$_5$)$_2$ | Cis | Base | — | C: 61.23  C: 59.6<br>H: 5.96  H: 5.5<br>N: 8.57  N: 8.7 |
| 1.168 | CH | 2,4-Cl$_2$C$_6$H$_3$ | 0 | | H | 0 | —N(C$_4$H$_9$)$_2$ | Cis | Base | — | C: 63.04  C: 63.1<br>H: 5.68  H: 5.6<br>N: 8.17  N: 7.8 |
| 1.169 | CH | 2,4-Cl$_2$C$_6$H$_3$ | 0 | | H | 0 | —N(—CH$_2$—CH—CH$_2$)$_2$ | Cis | Base | | |
| 1.170 | CH | 2,4-Cl$_2$C$_6$H$_3$ | 0 | | H | 0 | —NH—C$_4$H$_9$ | Cis | Base | 70–71 | C: 63.73  C: 63.5<br>H: 6.82  H: 6.7<br>N: 7.69  N: 7.8 |
| 1.171 | CH | 2,4-Cl$_2$C$_6$H$_3$ | 0 | | H | 0 | —NH—C$_8$H$_{17}$ | Cis | Base | | |
| 1.172 | CH | 2,4-Cl$_2$C$_6$H$_3$ | 0 | | H | 0 | 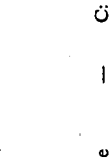 | Cis | Base | 157–158 | C: 57.99  C: 58.0<br>H: 4.87  H: 4.9<br>N: 8.82  N: 8.8 |
| 1.173 | CH | 2,4-Cl$_2$C$_6$H$_3$ | 0 | | H | 0 |  | Cis | Base | | |
| 1.174 | CH | 2,4-Cl$_2$C$_6$H$_3$ | 0 | | H$_3$C | 0 | —N(CH$_3$)$_2$ | Cis | Base | — | C: 60.51  C: 60.3<br>H: 5.71  H: 5.6<br>N: 8.82  N: 8.9 |
| 1.175 | CH | 2,4-Cl$_2$C$_6$H$_3$ | 0 | | H | 0 |  | Cis | Base | | |
| 1.176 | CH | 2,4-Cl$_2$C$_6$H$_3$ | 0 | | H | 1 | —NH—C$_4$H$_9$ | Cis | Base | | |

TABLE 1-continued
| | | | | | | | | |
|---|---|---|---|---|---|---|---|---|
| 1.177 | CH | 2,4-Cl$_2$C$_6$H$_3$ | 0 | 4 | H | 1 |  | Cis Base |
| 1.178 | CH | 2,4-Cl$_2$C$_6$H$_3$ | 0 | 4 | H | 1 |  | Cis Base |
| 1.179 | CH | 2,4-Cl$_2$C$_6$H$_3$ | 0 | 4 | H | 1 |  | Cis Base |
| 1.180 | CH | 2,4-Cl$_2$C$_6$H$_3$ | 0 | 4 | C$_3$H$_7$ | 0 | —N(C$_2$H$_5$)$_2$ | Cis Base |
| 1.181 | CH | 2,4-Cl$_2$C$_6$H$_3$ | 0 | 4 | H | 0 |  | Cis Base |
| 1.182 | CH | 2,4-Cl$_2$C$_6$H$_3$ | 0 | 4 | H | 0 |  | Cis Base C: 59.52 C: 59.1 H: 4.44 H: 4.2 N: 7.71 N: 7.6 |
| 1.183 | CH | 2,4-Cl$_2$C$_6$H$_3$ | 0 | 4 | H | 0 |  | Cis Base |
| 1.184 | CH | 2,4-Cl$_2$C$_6$H$_3$ | 0 | 4 | H | 0 |  | Cis Base |
| 1.185 | CH | 2,4-Cl$_2$C$_6$H$_3$ | 0 | 4 | H | 0 |  | Cis Base |

TABLE 1-continued

| | | | | | | | |
|---|---|---|---|---|---|---|---|
| 1.186 | CH | 2,4-Cl$_2$C$_6$H$_3$ | 0 | 2 | H | —NH—(2,4-Cl$_2$C$_6$H$_3$) | Cis | Base |
| 1.187 | CH | 2,4-Cl$_2$C$_6$H$_3$ | 0 | 4 | H | —NH—(4-OCH$_3$C$_6$H$_4$) | Cis | Base |
| 1.188 | CH | 2,4-Cl$_2$C$_6$H$_3$ | 0 | 4 | H | —NH—(2-Cl-6-CH$_3$C$_6$H$_3$) | Cis | Base |
| 1.189 | CH | 2,4-Cl$_2$C$_6$H$_3$ | 0 | 2 | H | —NH—(2,6-(CH$_3$)$_2$C$_6$H$_3$) | Cis | Base |
| 1.190 | CH | 2,4-Cl$_2$C$_6$H$_3$ | 0 | 4 | H | —N(CH$_3$)—(4-CH$_3$C$_6$H$_4$) | Cis | Base |
| 1.191 | CH | 2,4-Cl$_2$C$_6$H$_3$ | 0 | 4 | H | —N(CH$_3$)—C(O)—O—(4-ClC$_6$H$_4$) | Cis | Base |
| 1.192 | CH | 2,4-Cl$_2$C$_6$H$_3$ | 0 | 4 | H | —NH—C(O)—C(CH$_3$)$_3$ | Cis | .HNO$_3$ 158 C: 53.71 C: 53.5<br>H: 5.20 H: 5.2<br>N: 9.64 N: 9.3 |
| 1.193 | CH | 2,4-Cl$_2$C$_6$H$_3$ | 0 | 4 | H | —NH—C(O)—O—CH$_3$ | Cis | Base |

TABLE 1-continued

| No. | X | Ar | | R | | Group | | | mp | Analysis |
|---|---|---|---|---|---|---|---|---|---|---|
| 1.194 | CH | 2,4-Cl$_2$C$_6$H$_3$ | 0 | H | 0 | —NH—C(=O)—O—C$_2$H$_5$ | Cis | Base | | |
| 1.195 | CH | 2,4-Cl$_2$C$_6$H$_3$ | 0 | H | 1 | piperazine N—CH$_3$ | Cis | Base | 115–116 | C: 61.02 60.2<br>H: 6.07 6.1<br>N: 10.54 10.4 |
| 1.196 | CH | 2,4-Cl$_2$C$_6$H$_3$ | 0 | H | 1 | piperazine N—CH$_3$ | Cis | Base | Oil | C: 61.65 60.8<br>H: 6.28 6.1<br>N: 10.27 10.2 |
| 1.197 | CH | 2,4-Cl$_2$C$_6$H$_3$ | 0 | H | 2 | —N(CH$_3$)$_2$ | Cis | Base | Oil | C: 61.23 60.8<br>H: 5.96 5.9<br>N: 8.57 8.4 |
| 1.198 | CH | 2,4-Cl$_2$C$_6$H$_3$ | 0 | H | 2 | —N(C$_2$H$_5$)$_2$ | Cis | Base | | |
| 1.199 | CH | 2,4-Cl$_2$C$_6$H$_3$ | 0 | H | 1 | —N(C$_5$H$_2$)$_2$ | Cis | Base | | |
| 1.200 | CH | 2,4-Cl$_2$C$_6$H$_3$ | 0 | H | 1 | —N(C$_3$H$_7$)$_2$ | Cis | Base | | |
| 1.201 | CH | 2,4-Cl$_2$C$_6$H$_3$ | 0 | H | 1 | piperidine (cyclohexyl)$_2$ | Cis | Base | | |
| 1.202 | CH | 2,4-Cl$_2$C$_6$H$_3$ | 0 | H | 0 | piperazine N—CH$_3$ | Cis | Base | | |
| 1.203 | N | 2,4-Cl$_2$C$_6$H$_3$ | 0 | H | 0 | piperazine N—C$_2$H$_5$ | Cis | Base | | |
| 1.204 | CH | 2,4-Cl$_2$C$_6$H$_3$ | 0 | H | 0 | piperazine N—C$_4$H$_9$ | Cis | Base | | |
| 1.205 | CH | 2,4-Cl$_2$C$_6$H$_3$ | 0 | H | 0 | piperazine N—CH$_2$—CH=CH$_2$ | Cis | Base | — | C: 61.88 61.6<br>H: 5.94 6.1<br>N: 10.31 10.0 |

TABLE 1-continued

| | | | | | | | |
|---|---|---|---|---|---|---|---|
| 1.206 | CH | 2,4-Cl$_2$C$_6$H$_3$ | 0 | H | 0 | ![N-piperidine-C(=O)CH$_3$] | Cis | Base | — |
| 1.207 | CH | 2,4-Cl$_2$C$_6$H$_3$ | 4 | H | 0 | N-piperidine-CH$_2$-C(CH$_3$)$_2$-CH$_2$-CH$_3$... | Cis | Base | C: 59.45 C: 59.1 / H: 5.54 H: 5.6 / N: 10.27 N: 10.4 |
| 1.208 | CH | 2,4-Cl$_2$C$_6$H$_3$ | 4 | H | 0 | N-piperidine-phenyl | Cis | Base | |
| 1.209 | N | 2,4-Cl$_2$C$_6$H$_3$ | 4 | H | 0 | N-piperidine-(4-Cl-phenyl) | Cis | Base | |
| 1.210 | CH | 2,4-Cl$_2$C$_6$H$_3$ | 4 | H | 0 | N-piperidine-(4-F-phenyl) | Cis | Base | |
| 1.211 | CH | 2,4-Cl$_2$C$_6$H$_3$ | 4 | H | 0 | N-piperidine-(4-OCH$_3$-phenyl) | Cis | Base | |
| 1.212 | CH | 2,4-Cl$_2$C$_6$H$_3$ | 4 | H | 0 | N-piperidine-(4-O-C$_4$H$_9$-phenyl) | Cis | Base | |
| 1.213 | CH | 2,4-Cl$_2$C$_6$H$_3$ | 4 | H | 0 | N-piperidine-CH$_2$-phenyl | Cis | Base | |
| 1.214 | CH | 2,4-Cl$_2$C$_6$H$_3$ | 4 | H | 0 | | Cis | Base | |

TABLE 1-continued
| | | | | | | | | | |
|---|---|---|---|---|---|---|---|---|---|
| 1.215 | CH | 2,4-Cl$_2$C$_6$H$_3$ | 0 | 4 | H |  | Cis | Base | — | C: 61.20 C: 60.9<br>H: 5.30 H: 5.3<br>N: 8.92 N: 8.7 |
| 1.216 | CH | 2,4-Cl$_2$C$_6$H$_3$ | 0 | 4 | H | | Cis | Base | | |
| 1.217 | CH | 2,4-Cl$_2$C$_6$H$_3$ | 0 | 4 | H | | Cis | Base | | |
| 1.218 | CH | 2,4-Cl$_2$C$_6$H$_3$ | 0 | 4 | H | | Cis | Base | | |
| 1.219 | CH | 2,4-Cl$_2$C$_6$H$_3$ | 0 | 4 | H | | Cis | Base | | |
| 1.220 | CH | 2,4-Cl$_2$C$_6$H$_3$ | 0 | 4 | H | | Cis | Base | — | C: 59.44 C: 58.9<br>H: 4.57 H: 4.7<br>N: 11.55 N: 11.1 |
| 1.221 | CH | 2,4-Cl$_2$C$_6$H$_3$ | 0 | 4 | H | | Cis | Base | — | C: 61.48 C: 61.1<br>H: 5.57 H: 5.4<br>N: 8.60 N: 8.4 |
| 1.222 | CH | 2,4-Cl$_2$C$_6$H$_3$ | 0 | 4 | H | | Cis | Base | — | C: 62.15 C: 61.7<br>H: 5.82 H: 5.9<br>N: 8.36 N: 8.0 |

TABLE 1-continued

| # | | | | | | | Group | | | Calc | Found |
|---|---|---|---|---|---|---|---|---|---|---|---|
| 1.223 | N | 2,4-Cl$_2$C$_6$H$_3$ | 0 | — | 4 | H | —N⟨morpholine⟩ | Cis | Base | C: 59.53 H: 5.40 N: 8.33 | C: 59.4 H: 5.4 N: 8.2 |
| 1.224 | CH | 2,4-Cl$_2$C$_6$H$_3$ | 0 | — | 4 | H | —N⟨thiomorpholine⟩ | Cis | Base 107–108 | C: 57.69 H: 5.23 N: 8.07 | C: 57.5 H: 5.4 N: 7.7 |
| 1.225 | CH | 2,4-Cl$_2$C$_6$H$_3$ | 0 | — | 4 | H | —N⟨tetrahydroisoquinoline⟩ | Cis | Base | C: 65.46 H: 5.31 N: 7.63 | C: 65.1 H: 5.2 N: 7.2 |
| 1.226 | CH | 2,4-Cl$_2$C$_6$H$_3$ | 0 | — | 4 | H | —N(CH$_3$)—CH$_2$—C$_6$H$_5$ | Cis | Base | C: 64.69 H: 5.43 N: 7.80 | C: 64.8 H: 5.2 N: 7.8 |
| 1.227 | CH | 2,4-Cl$_2$C$_6$H$_3$ | 0 | — | 4 | H | —N(CH$_3$)—C$_6$H$_5$ | Cis | Base | C: 64.69 H: 5.43 N: 7.80 | C: 64.6 H: 5.6 N: 7.6 |
| 1.228 | CH | 2,4-Cl$_2$C$_6$H$_3$ | 0 | — | 4 | H | —N⟨piperazine-N—C$_6$H$_5$⟩ | Cis | Base | C: 64.25 H: 5.57 N: 9.67 | C: 63.5 H: 5.5 N: 9.5 |
| 1.229 | CH | 2,4-Cl$_2$C$_6$H$_3$ | 0 | — | 4 | H | —N⟨piperazine-N—C(O)C(CH$_3$)$_3$⟩ | Cis | Base | C: 61.33 H: 6.18 N: 9.54 | C: 61.8 H: 6.1 N: 9.2 |
| 1.230 | CH | 2,4-Cl$_2$C$_6$H$_3$ | 0 | — | 4 | H | —N⟨piperazine-N—C(O)—O—C$_2$H$_5$⟩ | Cis | Base | C: 58.44 H: 5.60 N: 9.74 | C: 57.7 H: 5.7 N: 9.3 |
| 1.231 | CH | 2,4-Cl$_2$C$_6$H$_3$ | 2 | 2,6-dimethyl | 4 | H | —NH—C$_8$H$_{17}$ | Cis | Base | | |
| 1.232 | CH | 2,4-Cl$_2$C$_6$H$_3$ | 2 | 2,6-dimethyl | 4 | H | —NH—C(O)—C$_6$H$_4$—Cl | Cis | Base | C: 59.96 H: 4.70 N: 6.70 | C: 60.3 H: 4.6 N: 6.5 |

TABLE 1-continued

| | | | | | | | |
|---|---|---|---|---|---|---|---|
| 1.233 | CH | 2,4-Cl$_2$C$_6$H$_3$ | 2 | 2,6-di-methyl | H | 0 | —NH—C(=O)—H | Cis | Base | — | C: 58.78 C: 58.5<br>H: 5.14 H: 5.2<br>N: 8.57 N: 8.3 |
| 1.234 | CH | 2,4-Cl$_2$C$_6$H$_3$ | 2 | 2,6-di-methyl | H | 0 | piperidine-N—C(=O)—H | Cis | Base | — | C: 60.11 C: 59.9<br>H: 5.76 H: 5.6<br>N: 10.01 N: 9.7 |
| 1.235 | CH | 2,4-Cl$_2$C$_6$H$_3$ | 2 | 2,6-di-methyl | H | 0 | piperidine-N—C(=O)—(2,4-Cl$_2$C$_6$H$_3$) | Cis | Base | — | C: 57.24 C: 57.2<br>H: 4.95 H: 4.9<br>N: 8.09 N: 7.8 |
| 1.236 | CH | 2,4-Cl$_2$C$_6$H$_3$ | 2 | 2,6-di-methyl | H | 0 | piperidine-N—C(=O)—N(CH$_3$)$_2$ | Cis | Base | — | C: 59.80 C: 60.0<br>H: 6.19 H: 6.3<br>N: 11.62 N: 11.4 |
| 1.237 | CH | 2,4-Cl$_2$C$_6$H$_3$ | 2 | 2,6-di-methyl | H | 0 | piperidine-N—C(=S)—S—CH$_3$ | Cis | Base | — | |
| 1.238 | CH | 2,4-Cl$_2$C$_6$H$_3$ | 0 | — | H | 0 | morpholine-N | Cis | Base | 110 | C: 59.53 C: 59.4<br>H: 5.40 H: 5.4<br>N: 8.33 N: 8.2 |
| 1.239 | CH | 2,4-Cl$_2$C$_6$H$_3$ | 2 | 2,6-di-methyl | H | 0 | 2-methyl-morpholine-N | Cis | Base | — | C: 62.14 C: 61.6<br>H: 6.29 H: 6.4<br>N: 7.50 N: 7.3 |
| 1.240 | CH | 2,4-Cl$_2$C$_6$H$_3$ | 2 | 2-chloro-6-methyl | H | 0 | 2,6-dimethyl-morpholine-N | Cis | Base | — | C: 57.89 C: 58.0<br>H: 5.55 H: 5.4<br>N: 7.23 N: 7.0 |

TABLE 1-continued

| | | | | | | | | | |
|---|---|---|---|---|---|---|---|---|---|
| 1.241 | CH | 2,4-Cl$_2$C$_6$H$_3$ | 2 | 2,6-di-methyl | 4 | H | thiomorpholine ring with CH$_3$ at 2,6 | Cis | Base | — | C: 60.41 C: 60.1<br>H: 6.12 H: 5.9<br>N: 7.29 N: 6.9 |
| 1.242 | CH | 2,4-Cl$_2$C$_6$H$_5$ | 2 | 2-chloro-6-methyl | 4 | H | thiomorpholine ring with CH$_3$ at 2,6 | Cis | Base | — | C: 56.33 C: 56.1<br>H: 5.40 H: 5.2<br>N: 7.04 N: 6.7 |

EXAMPLE 3

Cis-2-(2,4-dichlorophenyl)-2-(1H-imidazol-1-ylmethyl)-4-[4-chloro-2-(4-acetylpiperazin-1-ylmethyl)phenoxymethyl]-1,3-dioxolane A mixture consisting of 4.07 g=10 mmoles of cis-2-(2,4-dichlorophenyl)-2-(1H-imidazol-1-ylmethyl)-1,3-dioxolan-4-ylmethyl methanesulfonate, 2.7 g=10 mmoles of 4-chloro-2-(4-acetylpiperazin-1-ylmethyl)-phenol and 2.8 g=20 mmoles of potassium carbonate in 30 ml of dimethyl sulfoxide is heated for 16 hours at 100° C. and allowed to cool, the mixture is poured into 150 ml of water and extracted by shaking with twice 30 ml of methylene chloride, the combined methylene chloride phases are rinsed with 30 ml of water and dried over sodium sulfate and the solvent is removed in vacuo. The residue (5.3 g) is purified by column chromatography over silica gel using a 10:1 mixture of methylene chloride and ethanol as the migrating agent and is then dried over $P_4O_{10}$ at 50° C. in an oil pump vacuum. This gives 3.4 g (58% of theory) in the form of a highly viscous oil.

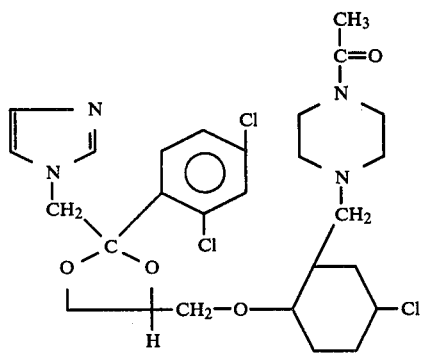

| | Analysis: | |
|---|---|---|
| | Calculated: | Found: |
| $C_{27}H_{29}Cl_3N_4O_4$ | C: 55.92 | C: 55.2 |
| | H: 5.04 | H: 5.1 |
| | N: 9.66 | N: 9.1 |

Molecular weight: 579.88.

Dimethylformamide, dimethylacetamide, methyl isobutyl ketone or N-methyl-2-pyrrolidone can also be used as the solvent in the same procedure as that described above.

EXAMPLE 4

Cis-2-(2,4-dichlorophenyl)-2-(1H-imidazol-1-ylmethyl)-4-[4-(N,N-dimethylaminomethyl)-phenoxymethyl]-1,3-dioxolane A solution of 1.8 g=10 mmoles of 4-(N,N-diethylaminomethyl)-phenol in 10 ml of absolute ethanol is added dropwise, at 20° C. and while stirring, to a freshly prepared solution of alcoholate consisting of 0.23 g=10 mmoles of sodium in 20 ml of absolute ethanol, stirring is continued for 10 minutes, 4.07 g=10 mmoles of cis-2-(2,4-dichlorophenyl)-2-(1H-imidazol-1-ylmethyl)-1,3-dioxolan-4-ylmethyl methanesulfonate are added in portions and the mixture is then boiled under reflux for 8 hours. After cooling, the solvent is removed in vacuo on a rotary evaporator, the residue is taken up in 50 ml of methylene chloride and 20 ml of 40% strength sodium hydroxide solution, the methylene chloride phase is washed twice with water and dried over sodium sulfate and the solvent is removed in vacuo. The residue (4.2 g) is purified by column chromatography over silica gel using a 20:1 mixture of methylene chloride and ethanol as the migrating agent, and is then dried as in Example 3. This gives 3.1 g (63% of theory) in the form of a highly viscous oil.

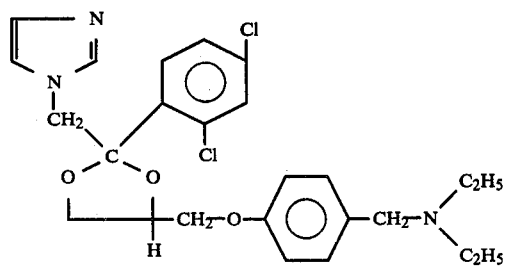

| | Analysis: | |
|---|---|---|
| | Calculated: | Found: |
| $C_{25}H_{29}Cl_2N_3O_3$ | C: 61.23 | C: 59.6 |
| | H: 5.96 | H: 5.5 |
| | N: 8.57 | N: 8.2 |

Molecular weight: 490.43.

EXAMPLE 5

Cis-2-(2,4-dichlorophenyl)-2-(1H-imidazol-1-ylmethyl)-4-[4-(N,N-dimethylaminoethyl)-phenoxymethyl]-1,3-dioxolane.

2.46 g=10 mmoles of 4-(N,N-dimethylaminoethyl)-phenol hydrobromide and 4.07 g=10 mmoles of cis-2-(2,4-dichlorophenyl)-2-(1H-imidazol-1-ylmethyl)-1,3-dioxolan-4-ylmethyl methanesulfonate are added in portions, successively, at 20° C. and while stirring, to a solution of alcoholate consisting of 0.46 g=20 mmoles of sodium in 30 ml of absolute ethanol, and the mixture is then boiled under reflux for 8 hours. Working up is carried out as described in Example 4. This gives 2.6 g (55% of theory) in the form of a highly viscous oil.

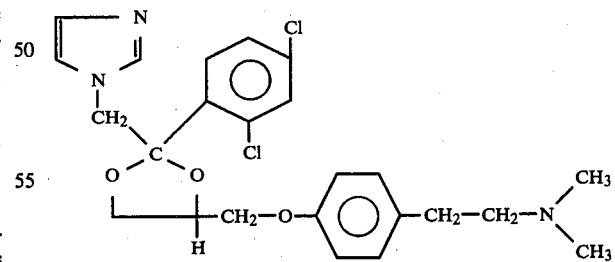

| | Analysis: | |
|---|---|---|
| | Calculated: | Found: |
| $C_{24}H_{27}Cl_2N_3O_3$ | C: 60.51 | C: 60.1 |
| | H: 5.71 | H: 5.7 |
| | N: 8.82 | N: 8.4 |

Molecular weight: 476.41.

EXAMPLE 6

Cis-2-(2,4-dichlorophenyl)-2-(1H-imidazol-1-ylmethyl)-4-[2,6-dimethyl-4-(4-phenylpiperazin-1-ylmethyl)-phenoxymethyl]-1,3-dioxolane and its dinitrate.

(a) Preparation of the free compound 3 g=10 mmoles of 2,6-dimethyl-4-(4-phenylpiperazin-1-ylmethyl)-phenol, and then 4.07 g=10 mmoles of cis-2-(2,4-dichlorophenyl)-2-(1H-imidazol-1-ylmethyl)-1,3-dioxolan-4-ylmethyl methanesulfonate are added in portions and while stirring to 10 ml of 50% strength sodium hydroxide solution, 40 ml of toluene and 0.3 g=0.9 mmole of tetrabutylammonium bromide, and the mixture is then boiled under reflux for 12 hours while stirring vigorously, the mixture is cooled and 30 ml of water are added, the aqueous phase is separated off, the organic phase is rinsed with water and dried over Na$_2$SO$_4$ and the solvent is removed in vacuo on a rotary evaporator. The crude product (6.1 g) is purified by column chromatography over silica gel using a 10:1 mixture of methylene chloride and ethanol as the migrating agent, or is used direct, as described below, for forming the salt. 5.1 g (85% of theory) are obtained in the form of a highly viscous, non-crystalline oil.

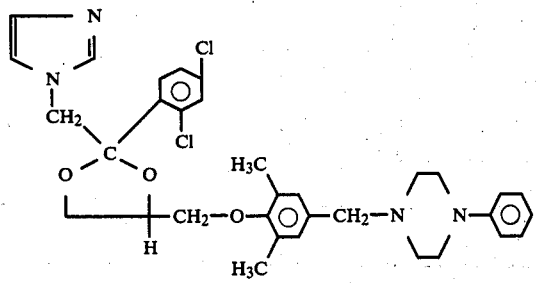

| | Analysis: | |
|---|---|---|
| | Calculated: | Found: |
| C$_{33}$H$_{36}$Cl$_2$N$_4$O$_3$ | C: 65.23 | C: 64.9 |
| | H: 6.0 | H: 6.2 |
| | N: 9.22 | N: 9.1 |

Molecular weight: 607.58.

(b) Precipitation of the dinitrate:

A solution of 0.28 ml=0.41 g=6.6 mmoles of 100% strength HNO$_3$ in 20 ml of ethyl acetate is added dropwise, at 20° C. and while stirring, to a solution in 60 ml of ethyl acetate of 2 g=3.3 mmoles of the oil described above, the mixture is allowed to stand at room temperature for 15 hours and is filtered and the residue is recrystallized from acetonitrile. This gives 1.3 g (53% of theory), melting at 145° C. (decomposition), of cis-2-(2,4-dichlorophenyl)-2-(1H-imidazol-1-ylmethyl)-4-[2,6-dimethyl-4-(4-phenylpiperazin-1-ylmethyl)-phenoxymethyl]-1,3-dioxolane, in the form of the dinitrate.

| | Analysis: | |
|---|---|---|
| | Calculated: | Found: |
| C$_{33}$H$_{38}$Cl$_2$N$_6$O$_9$ | C: 54.03 | C: 53.8 |
| | H: 5.22 | H: 5.3 |
| | N: 19.63 | N: 19.4 |

Molecular weight: 733.59.

EXAMPLE 7

Cis-2-(2,4-dichlorophenyl)-2-(1H-imidazol-1-ylmethyl)-4-[2-chloro-4-(N,N-dimethylaminomethyl)-6-methyl-phenoxymethyl]-1,3-dioxolane.

2 g=10 mmoles of 2-chloro-4-(N,N-dimethylaminomethyl)-6-methylphenol, and then 4.07 g=10 mmoles of cis-2-(2,4-dichlorophenyl)-2-(1H-imidazol-1-ylmethyl)-1,3-dioxolan-4-ylmethyl methanesulfonate are added in portions and while stirring to 10 ml of 50% strength sodium hydroxide solution, 40 ml of benzene and 0.3 g=1.3 mmoles of benzyltriethylammonium chloride, and the mixture is then boiled under reflux for 8 hours while stirring vigorously. Working up is carried out as described in Example 6a. This gives 3.8 g (75% of theory) in the form of a highly viscous, non-crystalline oil.

| | Analysis: | |
|---|---|---|
| | Calculated: | Found: |
| C$_{24}$H$_{26}$Cl$_3$N$_3$O$_3$ | C: 56.42 | C: 55.8 |
| | H: 5.13 | H: 5.2 |
| | N: 8.22 | N: 8.0 |

Molecular weight: 510.85.

EXAMPLE 8

Cis-2-(2,4-dichlorophenyl)-2-(1H-imidazol-1-ylmethyl)-4-[2-chloro-6-methyl-4-(piperazin-1-ylmethyl)-phenoxymethyl]-1,3-dioxolane.

A solution of 29.7 g=50 mmoles of the compound 1.135 (compare Table 1) and 8 g=0.2 mole of sodium hydroxide in a mixture of 100 ml of ethanol and 10 ml of water is boiled under reflux for 20 hours, the solvent is removed in vacuo on a rotary evaporator, the residue is taken up in water and the mixture is extracted with ether and the organic phase is dried over sodium sulphate and worked up as described in Example 1a. This gives 15.2 g (55% of theory) of a highly viscous, non-crystalline oil.

| | Analysis: | |
|---|---|---|
| | Calculated: | Found: |
| C$_{26}$H$_{29}$Cl$_3$N$_4$O$_3$ | C: 56.57 | C: 56.3 |
| | H: 5.30 | H: 5.2 |
| | N: 10.15 | N: 9.8 |

Molecular weight: 551.9.

EXAMPLE 9

The following compounds of the formula (Ib) are prepared in accordance with Example 8, but employing equivalent quantities of compounds of the formula (Ia-3).

TABLE 2

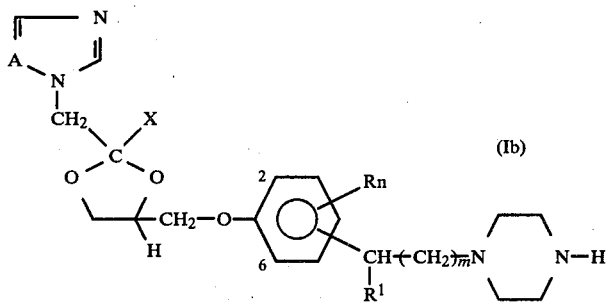

(Ib)

The explanations in Table 1 apply to 2,4-isomers and to v.

| Compound No. | A | X | n | Rn | v | R₁ | m | 2,4-Isomer | Melting point: [°C.] | Analysis Calculated: | | Found: | |
|---|---|---|---|---|---|---|---|---|---|---|---|---|---|
| 2.1 | CH | 2,4-Cl₂C₆H₃ | 2 | 2,6-dimethoxy | 4 | H | O | Cis | | | | | |
| 2.2 | CH | 2,4-Cl₂C₆H₃ | 2 | 2,6-dimethyl | 4 | H | O | Cis | | C: | 60.90 | C: | 60.7 |
| | | | | | | | | | | H: | 6.25 | H: | 6.2 |
| | | | | | | | | | | N: | 10.52 | N: | 10.5 |
| 2.3 | N | 2,4-Cl₂C₆H₅ | 2 | 2,6-dimethyl | 4 | H | O | Cis | | | | | |
| 2.4 | N | 2,4-Cl₂C₆H₃ | 2 | 2-chloro-6-methyl | 4 | H | O | Cis | | | | | |
| 2.5 | CH | 2,4-Cl₂C₆H₃ | 2 | 2,6-dichloro | 4 | H | O | Cis | | C: | 52.46 | C: | 52.3 |
| | | | | | | | | | | H: | 4.58 | H: | 4.4 |
| | | | | | | | | | | N: | 9.79 | N: | 9.8 |
| 2.6 | CH | 2,4-Cl₂C₆H₃ | O | — | 4 | H | O | Cis | | C: | 59.65 | C: | 59.2 |
| | | | | | | | | | | H: | 5.61 | H: | 5.7 |
| | | | | | | | | | | N: | 11.13 | N: | 10.8 |

EXAMPLE 10

Cis-2-(2,4-dichlorophenyl)-2-(imidazol-1-ylmethyl)-4-[2-chloro-4-(4-ethylthiocarbamoylpiperazin-1-ylmethyl)-6-methylphenoxymethyl]-1,3-dioxolane.

A solution of 0.9 g = 10 mmoles of ethyl isothiocyanate in 10 ml of toluene is added dropwise, at 20° C. and while stirring, to a solution of 5.5 g = 10 mmoles of the compound from Example 8 in 20 ml of toluene and 0.1 ml of triethylamine, and the mixture is then boiled under reflux for 5 hours. The solution is cooled, washed with water, dried with sodium sulfate and worked up as described in Example 1a.

This gives 5.2 g (81% of theory) of a highly viscous, non-crystalline oil.

| | Analysis: Calculated: | Found: |
|---|---|---|
| C₂₉H₃₄Cl₃N₅O₃S | C: 54.51 | C: 54.0 |
| | H: 5.36 | H: 5.3 |
| | N: 10.96 | N: 10.8 |

Molecular weight: 639.01

EXAMPLE 11

The following compounds (Ic) are prepared in accordance with Example 10, but employing equivalent quantities of compounds of the formula (Ib) and (IX):

TABLE 3

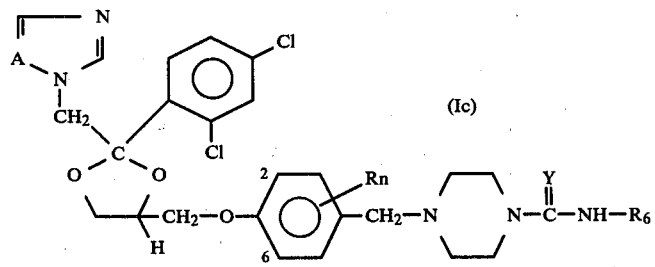

(Ic)

(a) The explanation in Table 1 applies to the 2,4-isomer.

| Compound No. | n | Rₙ | Y | R₆ | 2,4-Isomer | Melting point: [°C.] | Analysis Calculated: | | Found: | |
|---|---|---|---|---|---|---|---|---|---|---|
| 3.1 | 2 | 2-Cl 6-CH₃ | S | —CH₂—CH=CH₂ | Cis | — | C: | 59.65 | C: | 59.2 |
| | | | | | | | H: | 5.61 | H: | 5.4 |

TABLE 3-continued

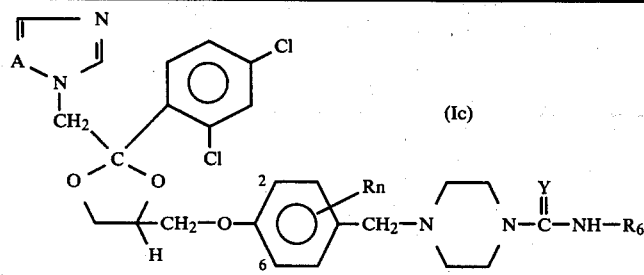

(a) The explanation in Table 1 applies to the 2,4-isomer.

| Compound No. | n | $R_n$ | Y | $R_6$ | 2,4-Isomer | Melting point: [°C.] | Analysis Calculated: | | Found: | |
|---|---|---|---|---|---|---|---|---|---|---|
| 3.2 | 2 | 2,6-dimethyl | S | $-CH_2-CH=CH_2$ | Cis | | N: | 11.13 | N: | 10.9 |
| 3.3 | 2 | 2,6-dimethyl | S | tert.-butyl | Cis | | | | | |
| 3.4 | 2 | 2-Cl 6-$CH_3$ | O | $-CH_3$ | Cis | — | C: H: N: | 55.32 5.14 11.52 | C: H: N: | 54.9 5.3 11.2 |
| 3.5 | 0 | — | O | $-C_4H_9$ | Cis | | | | | |
| 3.6 | 2 | 2,6-dichloro | S | $4-ClC_6H_4$ | Cis | | | | | |
| 3.7 | 2 | 2-Cl 6-$CH_3$ | O | $-C_6H_5$ | Cis | | | | | |
| 3.8 | 0 | — | O | $3-CF_3C_6H_4$ | Cis | | | | | |
| 3.9 | 2 | 2-Cl 6-$CH_3$ | O | $2,6-Cl_2C_6H_3$ | Cis | | | | | |
| 3.10 | 2 | 2,6-dimethyl | O | $4-CH_3C_6H_4$ | Cis | | | | | |

EXAMPLE 12

Cis-2-(2,4-dichlorophenyl)-2-(1H-imidazol-1-ylmethyl)-4-[4-(4-carbamoylpiperazin-1-ylmethyl)-2-chloro-6-methylphenoxymethyl]-1,3-dioxolane.

A mixture of 5.5 g=10 mmoles of the compound from Example 8, 1.2 g=15 mmoles of potassium cyanate and 20 ml of glacial acetic acid is stirred for 24 hours at 20° C., the solvent is removed in vacuo on a rotary evaporator, the residue is taken up in water, the mixture is extracted with methylene chloride, the organic phase is rinsed with 2 N sodium carbonate solution and the product is worked up as described in Example 1a. This gives 1.8 g (30% of theory) of a highly viscous, non-crystalline oil.

| | Analysis: Calculated: | | Found: | |
|---|---|---|---|---|
| $C_{27}H_{30}Cl_3N_5O_4$ | C: | 54.51 | C: | 54.1 |
| | H: | 5.08 | H: | 5.1 |
| | N: | 11.77 | N: | 11.5 |

Molecular weight: 594.93.

EXAMPLE 13

Cis-2-(2,4-dichlorophenyl)-2-(1H-imidazol-1-ylmethyl)-4-[2-chloro-4-(4-methoxycarbonylpiperazin-1-ylmethyl)-6-methylphenoxymethyl]-1,3-dioxolane and its dinitrate.

(a) Preparation of the free compound

A solution of 0.94 g=10 mmoles of chloroformic acid methyl ester in 10 ml of methylene chloride is added dropwise, while cooling at −10° C. and stirring, to a solution of 5.5 g=10 mmoles of the compound from Example 8 in 20 ml of methylene chloride and 10.1 g=10 mmoles of triethylamine, and the mixture is allowed to warm up to room temperature and is then boiled under reflux for 3 hours. The solution is cooled, washed with water, dried with sodium sulfate and worked up as described in Example 1a. This gives 5.1 g (85% of theory) of a highly viscous, non-crystalline oil.

| | Analysis: Calculated: | | Found: | |
|---|---|---|---|---|
| $C_{28}H_{31}Cl_3N_4O_5$ | C: | 55.14 | C: | 54.8 |
| | H: | 5.12 | H: | 5.2 |
| | N: | 9.18 | N: | 8.9 |

Molecular weight: 609.90

(b) Preparation of the dinitrate

Following the procedure of Example 1b, but employing equivalent quantities of the compound from Example 13a and nitric acid, gives 1.5 g (55% of theory), melting at 130° C., of cis-2-(2,4-dichlorophenyl)-2-(1H-imidazol-1-ylmethyl)-4-[2-chloro-4-(4-methoxycarbonylpiperazin-1-ylmethyl)-6-methylphenoxymethyl]-1,3-dioxolane in the form of the dinitrate.

| | Analysis: Calculated: | | Found: | |
|---|---|---|---|---|
| $C_{28}H_{33}Cl_3N_6O_{11}$ | C: | 45.70 | C: | 45.4 |
| | H: | 4.52 | H: | 4.8 |
| | N: | 11.42 | N: | 11.2 |

Molecular weight: 735.93

EXAMPLE 14

The following compounds (Id) are prepared in accordance with Example 13a, but employing equivalent quantities of compounds of the formula (Ib) and an acyl chloride derived from the corresponding carboxylic or sulfonic acid:

TABLE 4

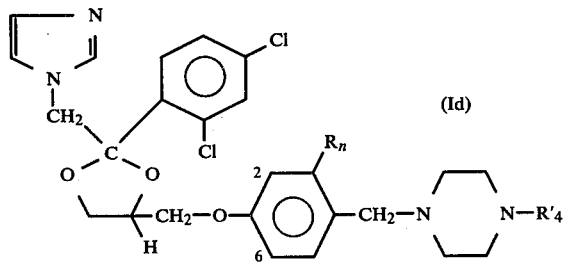

(Id)

The explanation in Table 1 applies to the 2,4-isomer

| Compound No. | n | Rn | R4 | 2,4-Isomer | Analysis Calculated: | Found: |
|---|---|---|---|---|---|---|
| 4.1 | 2 | 2-Cl; 6-$CH_3$ | —C(O)—tert.-butyl | Cis | | |
| 4.2 | 2 | 2,6-dimethyl | —C(O)—tert.-butyl | Cis | C: 62.44 H: 6.55 N: 9.10 | C: 62.0 H: 6.3 N: 8.9 |
| 4.3 | 2 | 2,6-dimethyl | —C(O)—$CH_2Cl$ | Cis | C: 57.29 H: 5.47 N: 9.22 | C: 57.1 H: 5.3 N: 9.0 |
| 4.4 | 2 | 2,6-dichloro | —C(O)—$CF_3$ | Cis | | |
| 4.5 | 2 | 2,6-dichloro | —$SO_2$—$C_2H_5$ | Cis | | |
| 4.6 | 2 | 2-Cl; 6-$CH_3$ | —C(O)—$N(CH_3)_2$ | Cis | | |
| 4.7 | 2 | 2-Cl; 6-$CH_3$ | —C(O)—$N(C_4H_9)_2$ | Cis | | |
| 4.8 | 0 | — | —C(O)—(2,4-dichlorophenyl) | Cis | | |
| 4.9 | 2 | 2,6-dimethyl | —C(O)—(4-chlorophenyl) | Cis | | |
| 4.10 | 2 | 2,6-dichloro | —C(O)—(3-$CF_3$-phenyl) | Cis | | |
| 4.11 | 2 | 2,6-dimethyl | —C(O)—(4-$CH_3$-phenyl) | Cis | | |
| 4.12 | 0 | — | —C(O)—(4-$OCH_3$-phenyl) | Cis | | |

TABLE 4-continued

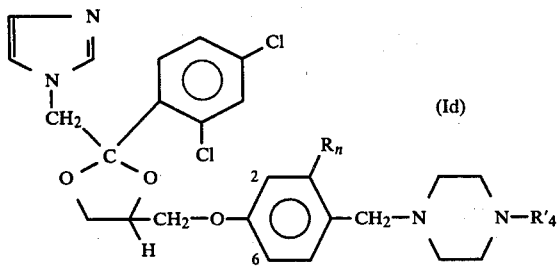

(Id)

The explanation in Table 1 applies to the 2,4-isomer

| Compound No. | n | Rn | R4 | 2,4-Isomer | Analysis Calculated: | Found: |
|---|---|---|---|---|---|---|
| 4.13 | 2 | 2,6-dichloro | —C(=O)—O—⟨phenyl⟩ | Cis | | |

EXAMPLE 15

Cis-2-(2,4-dichlorophenyl)-2-(1H-imidazol-1-ylmethyl)-4-[2-chloro-4-(4-formylpiperazin-1-ylmethyl)-6-methyl-phenoxymethyl]-1,3-dioxolane.

A solution of 5.5 g = 10 mmoles of the compound from Example 8 in 20 ml of formic acid ethyl ester is boiled under reflux for 24 hours and, after cooling, the solvent is removed in vacuo on a rotary evaporator. The residue is subjected to column chromatography as described in Example 1a. This gives 4.9 g (85% of theory) of a highly viscous, non-crystalline oil.

| | Analysis: | |
|---|---|---|
| | Calculated: | Found: |
| $C_{27}H_{29}Cl_3N_4O_4$ | C: 55.92 | C: 55.7 |
| | H: 5.04 | H: 5.1 |
| | N: 9.66 | N: 9.5 |

Molecular weight: 579.91

EXAMPLE 16

Cis-2-(2,4-dichlorophenyl)-2-(1H-imidazol-1-ylmethyl)-4-[2,6-dimethyl-4-(4-tert.-butoxycarbonylmethylpiperazin-1-ylmethyl)-phenoxymethyl]-1,3-dioxolane.

A mixture of 5.3 g = 10 mmoles of the compound 2.2 (compare Table 2), 2.8 g = 20 mmoles of potassium carbonate and 1.5 g = 10 mmoles of chloroacetic acid tert.-butyl ester in 20 ml of dimethylformamide is stirred for 6 hours at 80° C. Working up is carried out as described in Example 1a. This gives 3.5 g (55% of theory) of a highly viscous, non-crystalline oil.

| | Analysis: | |
|---|---|---|
| | Calculated: | Found: |
| $C_{33}H_{42}Cl_2N_4O_5$ | C: 61.39 | C: 61.2 |
| | H: 6.56 | H: 6.6 |
| | N: 8.68 | N: 8.6 |

Molecular weight: 645.63

EXAMPLE 17

The following compounds (Id') are prepared in accordance with Example 16, but employing equivalent quantities of the compounds from Example 8 and bromomethyl tert.-butyl ketone or chloroacetic acid N-butylamide:

Cis-2-(2,4-dichlorophenyl)-2-(1H-imidazol-1-ylmethyl)-4-[2-chloro-6-methyl-4-(4-tert.-butylcarboxymethylpiperazin-1-ylmethyl)-phenoxymethyl]-1,3-dioxolane.

4 g (62% of theory) of a highly viscous, non-crystalline oil are obtained.

| Analysis: | Calculated: C: 59.13 | Found: C: 58.9 |
|---|---|---|
| $C_{32}H_{39}Cl_3N_4O_4$ | H: 6.05 | H: 5.8 |
| | N: 8.62 | N: 8.5 |

Molecular weight: 650.05

Cis-2-(2,4-dichlorophenyl)-2-(1H-imidazol-1-ylmethyl)-4-[2-chloro-4-(4-butylaminocarboxymethylpiperazin-1-ylmethyl)-6-methylphenoxymethyl]-1,3-dioxolane.

2.1 g (32% of theory) of a highly viscous, non-crystalline oil are obtained.

| Analysis: | Calculated: C: 57.79 | Found: C: 57.5 |
|---|---|---|
| $C_{32}H_{40}Cl_3N_5O_4$ | H: 6.06 | H: 5.8 |
| | N: 10.53 | N: 10.1 |

Molecular weight: 665.06

EXAMPLE 18

Cis-2-(2,4-dichlorophenyl)-2-(1H-imidazol-1-ylmethyl)-4-[2,6-dimethyl-4-(4-hydroxyethylpiperazin-1-ylmethyl)-phenoxymethyl]-1,3-dioxolane.

Ethylene oxide is passed through a boiling solution of 10.6 g = 20 mmoles of the compound 2.2 (compare Table 2) in 50 ml of ethanol for 1 hour, the mixture is allowed to cool, the solvent is removed in vacuo and the residue is worked up as described in Example 3. This gives 4.8 g (42% of theory) of a highly viscous, non-crystalline oil.

| Analysis: | Calculated: C: 60.52 | Found: C: 60.6 |
|---|---|---|
| $C_{29}H_{36}Cl_2N_4O_4$ | H: 6.31 | H: 6.4 |

N: 9.74    N: 9.5

Molecular weight: 575.54

EXAMPLE 19

Cis-2-(2,4-dichlorophenyl)-2-(1H-imidazol-1-ylmethyl-4-[2,6-dimethyl-4-(4-butyloxyethylpiperazin-1-ylmethyl)-phenoxymethyl]-1,3-dioxolane.

A solution, in 10 ml of absolute dimethylformamide, of 5.75 g = 10 moles of the compound described above in Example 18 is added dropwise, while cooling and stirring, to a suspension of 0.3 g = 10 mmoles of sodium hydride (an 80% strength dispersion in oil) in 15 ml of absolute dimethylformamide at such a rate that the temperature does not exceed 20° C. Stirring is continued until the evolution of hydrogen is complete, a solution of 1.37 g = 10 mmoles of butyl bromide in 5 ml of absolute dimethylformamide is added dropwise at 20° C., and the mixture is then stirred for a further 6 hours at 80° C. After cooling, the mixture is worked up as described in Example 1a. This gives 3.8 g (60% of theory) of a highly viscous, non-crystalline oil.

| Analysis: | Calculated: C: 62.75 | Found: C: 62.5 |
|---|---|---|
| $C_{33}H_{44}Cl_2N_4O_4$ | H: 7.02 | H: 7.2 |
| | N: 8.87 | N: 8.6 |

Molecular weight: 631.65

EXAMPLE 20

Cis-2-(2,4-dichlorophenyl)-2-(1H-imidazol-1-ylmethyl)-4-[4-(4-butylpiperazin-1-ylmethyl)-phenoxymethyl]-1,3-dioxolane.

A mixture of 5.03 g = 10 mmoles of the compound 2.6 (compare Table 2), 0.72 g = 10 mmoles of butanal, 0.05 ml of concentrated sulfuric acid and 1 g of Raney nickel in 50 ml of absolute ethanol is stirred for 3 hours in an autoclave at 60° C. and under a hydrogen pressure of 100 atmospheres. After cooling, and releasing the pressure, the catalyst is filtered off, the solvent is removed in vacuo on a rotary evaporator, and the residue is taken up in methylene chloride, washed with 2 N sodium carbonate solution, dried with sodium sulfate and worked up as described in Example 1a. This gives 2.8 g (50% of theory) of a highly viscous, non-crystalline oil.

| Analysis: | Calculated: C: 62.31 | Found: C: 62.0 |
|---|---|---|
| $C_{29}H_{36}Cl_2N_4O_3$ | H: 6.49 | H: 6.5 |
| | N: 10.02 | N: 9.8 |

Molecular weight: 559.11

EXAMPLE 21

Cis-2-(2,4-dichlorophenyl)-2-(1H-imidazol-1-ylmethyl)-4-[2-chloro-6-methyl-4-(4-methylthiothiocarbonylpiperazin-1-ylmethyl)-phenoxymethyl]-1,3-dioxolane.

0.76 g = 10 mmoles of carbon disulfide are added dropwise, at 20° C. and while stirring, to a solution of 5.5 g = 10 mmoles of the compound from Example 8 in 30 ml of ethanol and 1 g = 10 mmoles of triethylamine, stirring is continued for a further 30 minutes and 1.26 g = 10 mmoles of dimethyl sulfate are then added dropwise at 20° C. and the mixture is stirred for a further hour at 20° C. and is then boiled under reflux for 1 hour. After cooling, the solvent is removed in vacuo, the residue is taken up in methylene chloride, the solution is washed with water and the organic phase is dried with sodium sulfate and worked up as described in Example 1a: This gives 3.8 g (60% of theory) of a highly viscous, non-crystalline oil.

| Analysis: | Calculated: C: 52.38 | Found: C: 52.1 |
|---|---|---|
| $C_{28}H_{31}Cl_3N_4O_3S$ | H: 4.86 | H: 4.8 |
| | N: 8.72 | N: 8.6 |

Molecular weight: 642.04

EXAMPLE 22

Cis-2-(2,4-dichlorophenyl)-2-(1H-imidazol-1-ylmethyl)-4-[4-(4-butylthiothiocarbonylpiperazin-1-ylmethyl)2,6-dimethylphenoxymethyl]-1,3-dioxolane.

The compound mentioned above is obtained in accordance with Example 21, but employing equivalent quantities of the compound 2.2 (compare Table 2), carbon disulfide and n-butyl bromide. 4.1 g (62% of theory) of a highly viscous, non-crystalline oil are obtained.

| Analysis: | Calculated: C: 57.91 | Found: C: 57.8 |
|---|---|---|
| $C_{32}H_{40}Cl_2N_4O_3S_2$ | H: 6.07 | H: 6.0 |
| | N: 8.44 | N: 8.5 |

Molecular weight: 663.70

EXAMPLE 23

(a) Preparation of the amino compound: cis-2-(2,4-dichlorophenyl)-2-(1H-imidazol-1-ylmethyl)-4-(4-aminomethylphenoxymethyl)-1,3-dioxolane.

A mixture of 47.6 g = 0.1 mole of the compound 1.172 (compare Table 1), 40 g = 0.5 mole of 50% strength sodium hydroxide solution and 400 ml of methylglycol is boiled under reflux for 12 hours, while stirring, the mixture is allowed to cool, the solvent is removed under an oil pump vacuum, the residue is taken up in methylene chloride, the mixture is rinsed three times with water, and the organic phase is dried with sodium sulfate and worked up as described in Example 1a. This gives 18 g (41% of theory) of a highly viscous, non-crystalline oil.

| Analysis: | Calculated: C: 58.07 | Found: C: 58.2 |
|---|---|---|
| $C_{21}H_{21}Cl_2N_3O_3$ | H: 4.87 | H: 5.0 |
| | N: 9.67 | N: 9.6 |

Molecular weight: 434.32

(b) Preparation of the isothiocyanate: cis-2-(2,4-dichlorophenyl)-2-(1H-imidazol-1-ylmethyl)-4-(4-isothiocyanatomethyl-phenoxymethyl)-1,3-dioxolane.

1 g = 13 mmoles of carbon disulfide is added dropwise, while cooling at −5° C. and stirring, to a solution, in 30 ml of pyridine, of 4.3 g = 10 mmoles of the above compound from Example 23a, stirring is continued for a further 30 minutes and 2.1 g = 10 mmoles of N,N'-dicyclohexylcarbodiimide are then added in portions at such a rate that the temperature does not exceed −5° C. The mixture is stirred for 2 hours at this temperature and then for a further hour at 25° C. and the solvent is removed under an oil pump vacuum. The residue is taken up in 20 ml of glacial acetic acid and 50 ml of water are added, while cooling at 10° C. and stirring. The precipitate which has been formed is filtered off and the filtrate is neutralized with sodium carbonate, while cooling at 10° C. and stirring, and is extracted by shaking with methylene chloride. The methylene chloride phase is dried over sodium sulfate and worked up as described in Example 1a. This gives 2.6 g (55% of theory) of a highly viscous, non-crystalline oil.

| Analysis: | Calculated: C: 55.47 | Found: C: 55.3 |
|---|---|---|
| $C_{22}H_{19}Cl_2N_3O_3S$ | H: 4.02 | H: 4.0 |
| | N: 8.82 | N: 8.6 |

Molecular weight: 476.38

EXAMPLE 24

The following compounds (Ig) can be prepared in accordance with Example 10, but employing equivalent quantities of the compound from Example 23a and appropriate compounds of the formula IX.

TABLE 5

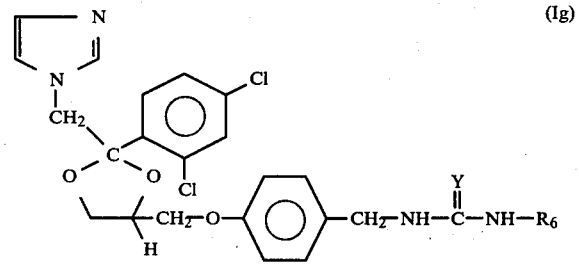
(Ig)

The explanation in Table 1 applies to the 2,4-isomer

| Compound No. | 2,4- Isomer | Y | $R_6$ | Analysis Calculated: | Found: | Melting point: [°C.] |
|---|---|---|---|---|---|---|
| 5.1. | Cis | S | $-CH_2-CH=CH_2$ | | | |
| 5.2. | Cis | S | $-tert.-butyl$ | | | |
| 5.3. | Cis | S | 4-Cl $C_6H_4$ | C:55.69 H: 4.17 N: 9.28 | C:55.7 H: 4.3 N: 9.3 | |
| 5.4. | Cis | O | 2,4-$Cl_2C_6H_3$ | | | |
| 5.5. | Cis | O | $C_6H_5$ | | | |

EXAMPLE 25

The following compounds (Ih) can be prepared in accordance with Example 13a, but employing equivalent quantities of the compound from Example 23a and an acyl chloride derived from the corresponding carboxylic acid.

TABLE 6

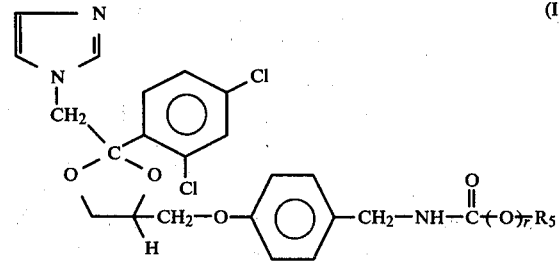
(Ih)

The explanation in Table 1 applies to the 2,4-isomer

| Compound No. | r | $R_5$ | 2,4- Isomer | Melting point [°C.] | Analysis Calculated: | Found: |
|---|---|---|---|---|---|---|
| 6.1. | O | $-CHCl_2$ | Cis | | | |
| 6.2. | O | 2,4-$Cl_2C_6H_3$ | Cis | | | |
| 6.3. | O | 3-$CF_3C_6H_4$ | Cis | | | |
| 6.4. | O | 4-Cl $C_6H_4$ | Cis | | C: 58.70 H: 4.22 N: 7.33 | C: 58.5 H: 4.2 N: 7.1 |
| 6.5. | O | 4-$CH_3C_6H_4$ | Cis | | | |

EXAMPLE 26

(a) Preparation of the N-formyl compound: cis-2-(2,4-dichlorophenyl)-2-(1H-imidazol-1-ylmethyl)-4-[4-(N-formylaminomethyl)-phenoxymethyl]-1,3-dioxolane.

The compound mentioned above is prepared in accordance with Example 15, but employing equivalent quantities of the compound of Example 23a. 4.1 g (90% of theory) of a highly viscous, non-crystalline oil are obtained.

| Analysis: | Calculated: C: 57.16 | Found: C: 57.2 |
|---|---|---|
| $C_{22}H_{21}Cl_2N_3O_4$ | H: 4.58 | H: 4.4 |
| | N: 9.09 | N: 8.9 |

Molecular weight: 462.33

(b) Preparation of the isonitrile:

A solution of 1.54 g=10 mmoles of phosphorus oxychloride in 5 ml of methylene chloride is added dropwise, while cooling at −10° C. and stirring, to a solution of 4.62 g=10 mmoles of the compound from Example 26a in 20 ml of methylene chloride and 2.5 g=25 mmoles of triethylamine, the mixture is allowed to warm up to 20° C. in the course of 1 hour and stirring is continued for a further 30 minutes. A solution of 2.6 g=25 mmoles of sodium carbonate in 20 ml of water is then added, stirring is continued for a further 30 minutes at 20° C., the organic phase is separated off and dried with sodium carbonate, and the solvent is removed in vacuo. The residue obtained (4.2 g) is purified by column chromatography over aluminum oxide (neutral), using methylene chloride as the migrating agent. This gives 2.9 g (65% of theory) of a highly viscous, non-crystalline oil.

| Analysis: | Calculated: C: 59.47 | Found: C: 59.5 |
|---|---|---|
| $C_{22}H_{19}Cl_2N_3O_3$ | H: 4.31 | H: 4.2 |
| | N: 9.46 | N: 9.5 |

Molecular weight: 444.30

Preparation of the starting materials

The preparation of compounds of the general formula (II)

EXAMPLE 27

The following compounds of the general formula (II) are prepared in analogy with J.Med.Chem. 1979, 22, page 1003 and Example 38 of German Offenlegungsschrift No. 2,804,096, (compare, in this context, the reaction sequence (XV)→(XVII)→(XVI)→(XVIII)→(XIX)→(XX)→(II′) in the general reaction diagram).

TABLE 7

(II)

The explanation in Table 1 applies to the 2,4-isomer

| Compound No. | A | X | 2,4-Isomer | Melting point: [°C.] |
|---|---|---|---|---|
| 7.1. | CH |  | Cis | 91–92 |
| 7.2. | CH |  | Trans | |
| 7.3. | N | 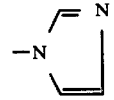 | Cis | 98 |

TABLE 7-continued

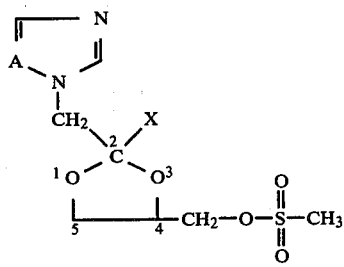
(II)

The explanation in Table 1 applies to the 2,4-isomer

| Compound No. | A | X | 2,4-Isomer | Melting point: [°C.] |
|---|---|---|---|---|
| 7.4. | N | 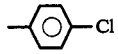 | Cis | 116 |

The preparation of compounds of the general formula (III)

EXAMPLE 28

4-(4-Acetylpiperazin-1-ylmethyl)-2,6-dimethylphenol

A solution of 35.8 g=0.2 mole of 2,6-dimethyl-4-(N,N-dimethylaminomethyl)-phenol and 25.6 g=0.2 mole of acetylpiperazine in 100 ml of xylene is boiled under reflux for 5 hours, in the course of which nitrogen is passed through the solution. After cooling, the precipitate is filtered off, washed with ethyl acetate and dried over phosphorus pentoxide in vacuo. This gives 46.1 g (88% of theory), melting point: 150°–151° C.

EXAMPLE 29

The following compounds of the general formula (III) are prepared in accordance with Example 28, but employing equivalent quantities of a corresponding N,N-dimethylaminomethylphenol Mannich base and an amino compound of the general formula (XII)

TABLE 8

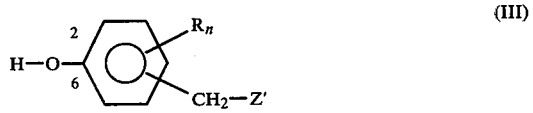
(III)

| Compound No. | v$^{(a)}$ | n | $R_n$ | Z′ | Melting point: [°C.] |
|---|---|---|---|---|---|
| 8.1. | 2 | 1 | 4-Cl | 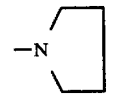 | 171 |
| 8.2. | 2 | 1 | 4-Cl | 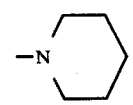 | 63–66 |
| 8.3. | 2 | 1 | 4-Cl |  | 54–55 |

TABLE 8-continued $$\underset{6}{\overset{2}{H-O}}\underbrace{\phantom{XXX}}_{CH_2-Z'}^{R_n} \quad (III)$$

| Compound No. | ν(a) | n | $R_n$ | Z' | Melting point: [°C.] |
|---|---|---|---|---|---|
| 8.4. | 2 | 1 | 4-Cl | −N⟨N=⟩ (imidazole) | 170–172 |
| 8.5. | 2 | 1 | 4-tert.-butyl | −N⟨N=⟩ (imidazole) | 157 |
| 8.6. | 2 | 1 | 4-O—CH₃ | −N⟨N=⟩ (imidazole) | 165 |
| 8.7. | 2 | 1 | 4-C(=O)—O—C₂H₅ | −N⟨N=⟩ (imidazole) | 194 |
| 8.8. | 2 | 1 | 4-O-(2,4-dichlorophenyl) | −N⟨N=⟩ (imidazole) | 230–232 |
| 8.9. | 2 | 2 | 4,6-Cl₂ | −N⟨N=⟩ (imidazole) | 181–183 |
| 8.10. | 2 | 2 | 4,6-Cl₂ | −N⟨N=N⟩ (triazole) | 187–188 |
| 8.11. | 1 | 2 | 4-Cl | −N⟨N=N⟩ (triazole) | 190 |
| 8.12. | 2 | 1 | −C(CH₃)₂—CH₂—C(CH₃)₂—CH₃ | −N⟨N=⟩ (imidazole) | 176 |
| 8.13. | 2 | 2 | 4,6-Cl₂ | −N(piperazinyl)N—CH₃ | 105 |
| 8.14. | 4 | 2 | 2,6-dimethyl | −N(C₂H₅)₂ | 58–59 |
| 8.15. | 4 | 2 | 2,6-dimethyl | −N(piperazinyl)N—SO₂—CH₃ | 166–167 |

TABLE 8-continued $$\text{H}-\text{O}-\underset{6}{\overset{2}{\bigcirc}}\overset{R_n}{\underset{CH_2-Z'}{}}\quad (III)$$

| Compound No. | v$^{(a)}$ | n | R$_n$ | Z' | Melting point: [°C.] |
|---|---|---|---|---|---|
| 8.16. | 4 | 2 | 2,6-dimethyl | —N(piperazine)N-phenyl | 115–116 |
| 8.17. | 4 | 2 | 2-chloro-6-methyl | —N(CH$_3$)$_2$ | 110–112 |
| 8.18. | 4 | 2 | 2-chloro-6-methyl | —N(piperazine)N—CH$_3$ | 105 |
| 8.19. | 4 | 2 | 2-chloro-6-methyl | —N(piperazine)N—C(O)—CH$_3$ | 150–152 |
| 8.20. | 4 | 2 | 2-chloro-6-methyl | —N(imidazole) | 163–165 |
| 8.21. | 4 | 2 | 2-chloro-6-methyl | —N(thiomorpholine)S | 108–110 |
| 8.22. | 4 | 2 | 2-chloro-6-methyl | —N(tetrahydroisoquinoline) | 116 |
| 8.23. | 4 | 2 | 2,6-dichloro | —N(CH$_3$)$_2$ | 180–183 |
| 8.24. | 4 | 2 | 2,6-dichloro | —N(imidazole) | 204 |
| 8.25. | 4 | 2 | 2,6-dimethyl | —N(2,6-dimethylmorpholine) CH$_3$* ... CH$_3$ | 119–131 |
| 8.26. | 4 | 2 | 2-chloro-6-methyl | —N(2,6-dimethylmorpholine) CH$_3$* ... CH$_3$ | 124–136 |

TABLE 8-continued (III)

H—O—⟨benzene with positions 2, 6, $R_n$, $CH_2$—Z'⟩

| Compound No. | v(a) | n | $R_n$ | Z' | Melting point: [°C.] |
|---|---|---|---|---|---|
| 8.27 | 4 | 2 | 2,6-dimethyl | —N(CH(CH₃)CH₂)₂S (CH₃*) | 125–138 |
| 8.28 | 4 | 2 | 2-chloro-6-methyl | —N(CH(CH₃)CH₂)₂S (CH₃*) | 125–138 |
| 8.29 | 4 | 2 | — | —N(CH(CH₃)CH₂)₂O (CH₃*) | 98–106 |
| 8.30 | 4 | 2 | 2,6-dimethyl | —N(CH=CH)N (imidazolyl) | 171–172 |

*mixture of cis and trans isomers
(a)In the Table, v indicates the position of the radical —CH₂—Z'.

EXAMPLE 30

4-(4-Acetylpiperazin-1-ylmethyl)-phenol

A mixture of 22.4 g=0.2 mole of p-hydroxybenzaldehyde, 25.6 g=0.2 mole of acetylpiperazine, 200 ml of methanol, 10 g of Raney nickel and 0.1 ml of concentrated sulfuric acid is stirred for 4 hours in an autoclave at 80° C. and under a hydrogen pressure of 100 atmospheres. After cooling, and releasing the pressure, the catalyst is filtered off, the solvent is removed in vacuo on a rotary evaporator, the residue is taken up in methylene chloride, the mixture is washed with 2 N sodium carbonate solution, the organic phase is dried with sodium sulfate, the solvent is removed as above and the residue is recrystallized from a mixture of ethyl acetate and diisopropyl ether. This gives 33.4 g (71% of theory), melting point: 130°–132° C.

EXAMPLE 31

4-Hydroxybenzylamine

Ammonia is passed into 500 ml of ethanol at 10° C. until saturation is reached, 122.1 g=1 mole of p-hydroxybenzaldehyde, 20 g of Raney nickel and 0.1 ml of concentrated sulfuric acid are added and the mixture is stirred in an autoclave for 6 hours at room temperature and under a hydrogen pressure of 100 atmospheres. After releasing the pressure, the catalyst is filtered off and the filtrate is boiled up with active charcoal, filtered and concentrated. The residue is recrystallized from a mixture of ethanol and ether. This gives 104 g (85% of theory), melting point: 104° C.

EXAMPLE 32

(a) Preparation of the bisacetyl compound: acetic acid (4-acetoxybenzyl)-amide 22.44 g=0.22 mole of acetic anhydride are added dropwise to a solution of 12.3 g=0.1 mole of 4-hydroxybenzylamine in 20 ml of pyridine at such a rate that the temperature does not exceed 60° C., stirring is then continued for a further hour at this temperature, the solvent is removed in vacuo, the residue is taken up in water, the mixture is extracted with methylene chloride, the organic phase is dried over sodium sulfate, the solvent is removed in vacuo and the residue is recrystallized from a mixture of toluene and ether. This gives 14.65 g (73% of theory), melting point: 82°–83° C.

(b) Preparation of the monoacetyl compound: acetic acid (4-hydroxybenzyl)-amide 20.7 g=0.1 mole of acetic acid (4-acetoxybenzyl)-amide are introduced in portions, at 25° C. and while stirring, into a solution of 8.8 g of 50% strength sodium hydroxide solution=0.11 mmole in 300 ml of ethanol, stirring is continued for a further 2 hours and the solvent is removed in vacuo. The residue is taken up in a 1:1 mixture of methylene chloride and ethanol, the mixture is filtered through silica gel and the filtrate is concentrated. The residue is recrystallized from ethyl acetate. This gives 14 g (85% of theory), melting point: 137° C.

EXAMPLE 33

(a) Preparation of 4-(piperidin-1-ylethyl)-anisole:

A solution of 28 g=0.12 mole of 4-methoxyphenylacetic acid piperidide in 100 ml of absolute ether is added dropwise, while stirring, to a suspension of 4.6 g=0.12 mole of lithium aluminum hydride in 250 ml of absolute ether at such a rate that the ether boils gently; the mixture is then boiled under reflux for 6 hours. 12 ml=0.67 mole of water are added dropwise cautiously, while cooling and stirring, the stirring is then switched off and the mixture is filtered after 16 hours, the filter residue is washed with ether, the filtrate is evaporated in vacuo and the residue is distilled under an oil pump vacuum. This gives 20.0 g (76% of theory), boiling point/0.2 mm Hg 96°–98° C.

(b) Preparation of 4-(piperidin-1-ylethyl)-phenol

A solution of 11 g=50 mmoles of 4-(piperidin-1-ylethyl)-anisole in a mixture of 50 ml of glacial acetic acid and 50 ml of 48% strength hydrobromic acid is boiled under reflux for 4 hours, the solution is evaporated in vacuo and the residue is recrystallized from ethanol. This gives 9 g of the hydrobromide, melting point: 265° C. The salt is dissolved in 30 ml of water and the free base is precipitated with concentrated aqueous ammonia solution and is filtered off. This gives 5.5 g (54% of theory), melting point: 168°–169° C.

EXAMPLE 34

The following hydroxyphenylalkylamines are obtained in accordance with Example 33a and b, but employing equivalent quantities of corresponding methoxyphenylacetic or methoxyphenylpropionic acid amides, lithium aluminum hydride and glacial acetic acid/hydrobromic acid: 4-(4-methylpiperazin-1-ylethyl)-phenol (melting point: 125°–126° C.), 4-(N,N-dimethylaminopropyl)-phenol (melting point: 109°–110° C.) and 4-(4-methylpiperazin-1-ylpropyl)-phenol (melting point: 137°–138° C.).

Examples of the Second Process of Preparation According to Claim 3

EXAMPLE 35

(a) Preparation of a compound of the general formula (V)

2-Bromomethyl-2-(4-chlorophenyl)-4-[2-chloro-4-(N,N-dimethylaminomethyl)-6-methylphenoxymethyl]-1,3-dioxolane.

4 g=20 mmoles of 2-chloro-4-(N,N-dimethylaminomethyl)-6-methylphenol are added in portions, while cooling with an ice bath and stirring, to a suspension of 0.6 g=20 mmoles of sodium hydride (an 80% strength dispersion in oil) in 30 ml of absolute dimethylformamide at such a rate that the temperature does not exceed 20° C. Stirring is continued at 20° C. until the evolution of hydrogen is complete, 8.26 g=20 mmoles of 2-bromomethyl-2-(4-chlorophenyl)-1,3-dioxolan-4-ylmethyl methanesulfonate (compound of the formula (IV)) are then introduced in portions, stirring is continued for 7 hours at 60° C. and the mixture is worked up as described in Example 1a. This gives 7 g (71% of theory) of a highly viscous, noncrystalline oil.

| Analysis: | Calculated: C: 51.56 | Found: C: 51.6 |
|---|---|---|
| $C_{21}H_{24}BrCl_2NO_3$ | H: 4.94 | H: 5.0 |
| | N: 2.86 | N: 2.5 |

Molecular weight: 489.24

(b) Preparation of a compound of the general formula (I): 2-(4-chlorophenyl)-2-(1H-imidazo-1-ylmethyl)-4-[2-chloro-4-(N,N-dimethylaminomethyl)-6-methylphenoxymethyl]-1,3-dioxolane.

0.68 g=10 mmoles of imidazole is added, while cooling and stirring, to a suspension of 0.3 g=10 mmoles of sodium hydride (an 80% strength dispersion in oil) in 20 ml of dimethylacetamide at such a rate that the temperature does not exceed 20° C., stirring is continued until the evolution of hydrogen is complete, a solution, in 5 ml of dimethylacetamide, of 4.9 g=10 mmoles of the compound from Example 35a is added, the mixture is then boiled under reflux for 24 hours and is worked up as described in Example 1a. This gives 1.7 g (35% of theory) of a highly viscous, non-crystalline oil.

| Analysis: | Calculated: C: 60.56 | Found: C: 60.6 |
|---|---|---|
| $C_{24}H_{27}Cl_2N_3O_3$ | H: 5.71 | H: 5.7 |
| | N: 8.82 | N: 8.9 |

Molecular weight: 476.40

EXAMPLE 36

2-(4-Chlorophenyl)-2-(1H-imidazol-1-ylmethyl)-4-[4-(4-acetylpiperazin-1-ylmethyl)-2-chloro-6-methylphenoxymethyl]-1,3-dioxolane 2.8 g=10 mmoles of 4-(4-acetylpiperazin-1-ylmethyl)-2-chloro-6-methylphenol are added in portions, while cooling and stirring, to a suspension of 0.3 g=10 mmoles of sodium hydride (an 80% strength dispersion in oil) in 20 ml of dimethylacetamide at such a rate that the temperature does not exceed 20° C. 4.1 g=10 mmoles of 2-bromomethyl-2-(4-chlorophenyl)-1,3-dioxolan-4-ylmethyl methanesulfonate are then introduced in portions and stirring is continued for 6 hours at 80° C. 0.8 g=5 mmoles of potassium iodide and 0.9 g=10 mmoles of the sodium salt of imidazole are introduced at this temperature and the mixture is then stirred for 48 hours at 160° C. and worked up as described in Example 1a. This gives 2 g (35% of theory) of a highly viscous, non-crystalline oil.

| Analysis: | Calculated: C: 60.11 | Found: C: 59.9 |
|---|---|---|
| $C_{28}H_{32}Cl_2N_4O_4$ | H: 5.77 | H: 5.5 |
| | N: 10.01 | N: 9.7 |

Molecular weight: 559.6

EXAMPLE 37

The following compounds of the general formula (I) can be prepared in accordance with Example 36, but employing equivalent quantities of compounds of the general formula (IV), (III) and (VI).

TABLE 9

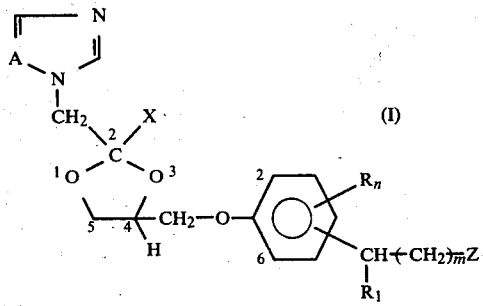

(I)

The explanations in Table 1 apply to v and the 2,4-isomer.

| Compound No. | A | X | n | $R_n$ | v | $R_1$ | m | Z | 2,4-Isomer | Base or salt | Melting point: [°C.] | Analysis Calculated: | Found: |
|---|---|---|---|---|---|---|---|---|---|---|---|---|---|
| 9.1 | CH | 4-Cl—C$_6$H$_4$ | 2 | 2,6-dimethyl | 4 | H | 0 | —N⏝N—C(=O)—CH$_3$ | | Base | | C: 64.61 H: 6.54 N: 10.39 | C: 64.3 H: 6.5 N: 10.1 |
| 9.2 | H | 2,4-Cl$_2$C$_6$H$_3$ | 2 | 2,6-dichloro | 4 | H | 0 | —N(C$_2$H$_5$)$_2$ | cis | Base | | C: 50.27 H: 4.95 N: 10.20 | C: 50.0 H: 5.0 N: 9.8 |
| 9.3 | CH | 2,4-Cl$_2$C$_6$H$_3$ | 0 | | 4 | H | 0 | —N(C$_2$H$_5$)$_2$ | cis | Base | — | C: 61.23 H: 5.96 N: 8.57 | C: 59.6 H: 5.5 N: 8.7 |
| 9.4 | CH | 2,4-Cl$_2$C$_6$H$_3$ | 0 | | 4 | H | 0 | —N(CH$_3$)(C(=O))—C$_8$H$_{17}$ | cis | Base | — | C: 63.26 H: 6.68 N: 7.14 | C: 63.2 H: 6.9 N: 7.2 |
| 9.5 | N | 2,4-Cl$_2$C$_6$H$_3$ | 2 | 2-Cl; 6-CH$_3$ | 4 | H | 0 | —N⏝N—CH$_2$—C$_6$H$_4$—Cl | cis | Base | | | |
| 9.6 | CH | 4-BrC$_6$H$_4$ | 2 | 2-Cl; 6-CH$_3$ | 4 | H | 0 | —N(C$_2$H$_5$)$_2$ | | Base | | | |
| 9.7 | CH | 2,4-Cl$_2$C$_6$H$_3$ | 0 | | 4 | H | 1 | —N⏝ (piperidine) | cis | Base | 151–152 | C: 62.79 H: 6.05 N: 8.14 | C: 62.3 H: 6.1 N: 8.0 |

In addition, the following compounds of the general formula (I) are prepared in analogy with Example 36: Compound No.: 1.95, 1.135, 1.156, 1.172 and 1.207 (compare Table 1).

Preparation of the Starting Materials

The preparation of compounds of the general formula (IV)

EXAMPLE 38

(a) Preparation of a compound of the general formula (XVI) (compare reaction diagram): 2-bromomethyl-2-(4-chlorophenyl)-4-hydroxymethyl-1,3-dioxolane A solution of 309.2 g=2 moles of 4-chloroacetophenone and 10 g=0.06 mole of p-toluenesulfonic acid in a mixture of 800 ml of benzene, 400 ml of n-butanol and 201.5 g=2.2 moles of glycerol is boiled under a water separator for 48 hours, the solution is cooled to 30° C., 351.6 g=112 ml=2.2 moles of Br$_2$ are added dropwise at this temperature in the course of 2.5 hours, while stirring, and the solvent is then removed in vacuo on a rotary evaporator. The residue is taken up in 800 ml of methylene chloride and washed with 6 N sodium hydroxide solution, while cooling, the organic phase is dried with sodium sulfate and the solvent is removed in vacuo. This gives 580 g (94% of theory) of a viscous oil.

(b) Preparation of a compound of the general formula (IV): 2-bromomethyl-2-(4-chlorophenyl)-1,3-dioxolan-4-ylmethyl methanesulfonate 50.4 g=0.44 mole of methanesulfochloride are added dropwise, at 0° C. and while stirring, to a solution of 123 g=0.4 mole of the compound from Example 38a in 150 ml of pyridine, the mixture is allowed to warm up to 25° C. and stirring is continued for a further 4 hours. The reaction mixture is poured into 1 l of ice water and extracted with methylene chloride, the organic phase is washed with half-concentrated hydrochloric acid, while cooling, and is dried over sodium carbonate, the solvent is removed in vacuo, the residue is taken up in methanol and the precipitate is filtered off and recrystallized from methanol. This gives 64.7 g (42% of theory), melting point: 107°–108° C.

EXAMPLE 39

The following compounds of the general formula (IV) can be prepared in accordance with Example 38b, but employing equivalent quantities of compounds of the formula (XVI) and corresponding sulfonic acid chlorides:

Examples of the Third Process of Preparation According to Claim 4

EXAMPLE 40

Cis-trans-2-(2,4-dichlorophenyl)-2-(1H-imidazol-1-ylmethyl)-4-[2-chloro-4-(N,N-dimethylaminomethyl)-6-methylphenoxymethyl]-1,3-dioxolane.

A mixture of 30 ml of xylene, 20 ml of methylglycol and 8 g=42 mmoles of p-toluenesulfonic acid.$H_2O$ is first boiled under a water separator until it is free from water. The solution is then cooled and 5.1 g=20 mmoles of 2,4-dichlorophenylimidazol-1-yl methyl ketone and 5.5 g=20 mmoles of 1-[2-chloro-4-(N,N-dime-

TABLE 10

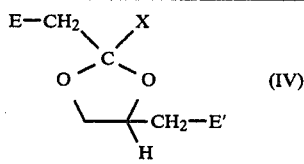

(IV)

Cis and trans relate to the E—$CH_2$— and E'—$CH_2$— radicals in the 2-position and 4-position, respectively, of the dioxolane ring.

| Compound No. | E | E' | X | 2,4-Isomer | Melting point [°C.] | Analysis Calculated: | Analysis Found: |
|---|---|---|---|---|---|---|---|
| 10.1. | Br | —O—$SO_2$—$CH_3$ | 2,4-$Cl_2C_6H_3$ | Cis | 84 | C: 34.31 H: 3.12 | C: 34.1 H: 3.2 |
| 10.2. | Br | —O—$SO_2$—C$_6$H$_4$—$CH_3$ | 2,4-$Cl_2C_6H_3$ | Cis | Oil | C: 43.57 H: 3.45 | C: 43.4 H: 3.5 |
| 10.3. | Br | —O—$SO_2$—$CH_3$ | 4-Br$C_6H_4$ | | | | |
| 10.4. | Br | —O—$SO_2$—$CH_3$ | 2,4-$Cl_2C_6H_3$ | Trans | | | |
| 10.5. | Br | —O—$SO_2$—C$_6$H$_4$—Cl | 4-$CH_3C_6H_4$ | | | | |
| 10.6. | Br | —O—$SO_2$—$CH_3$ | naphthyl | | | | |
| 10.7. | Br | —O—$SO_2$—C$_6$H$_4$—Cl | Cl-thienyl-CH$_3$ | | | | |
| 10.8. | Cl | —O—$SO_2$—$CH_3$ | 2,4$Cl_2C_6H_3$ | Cis | | | |
| 10.9. | Br | —O—$SO_2$—C$_6$H$_4$—Cl | 4-$CH_3$—O—$C_6H_4$ | | | | |
| 10.10. | Br | —O—$SO_2$—$CH_3$ | 4-F$C_6H_4$ | | 79–80 | C: 39.04 H: 3.82 | C: 39.0 H: 3.8 |
| 10.11. | Br | —O—$SO_2$—C$_6$H$_4$—Cl | 4-$CF_3$—$C_6H_4$ | | | | | thylaminomethyl)-6-methylphenoxy]-2,3-propanediol are added and the mixture is boiled under a water separator for a further 48 hours. After cooling, the solvent is removed in vacuo, the residue is taken up in 50 ml of 2 N sodium hydroxide solution, the mixture is extracted with methylene chloride and the organic phase is dried with sodium sulfate and worked up as described in Example 1a. This gives a highly viscous, non-crystalline oil.

| Analysis: | Calculated: C: 56.42 | Found: C: 55.8 |
|---|---|---|
| $C_{24}H_{26}Cl_3N_3O_3$ | H: 5.13 | H: 5.2 |
| | N: 8.26 | N: 8.0 |

Molecular weight: 510.85

EXAMPLE 41

The following compounds of the general formula (I) are prepared in accordance with Example 40, but employing equivalent quantities of 2,4-dichlorophenylimidazol-1-yl methyl ketone and corresponding propane-2,3-diols: Compound No.: 1.135, 1.172 and 1.207 (compare Table 1).

We claim:
1. A 1-(1,3-dioxolan-2-ylmethyl)-azole of the formula (I)

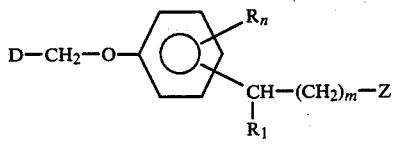

and its stereoisomers and its salts with a physiologically acceptable acid, in which D denotes a 1-(1,3-dioxolan-2-ylmethyl)-azole radical of the following structure

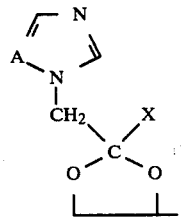

in which A denotes nitrogen or methine and X denotes naphthyl, thienyl, halogenothienyl or a phenyl group optionally carrying 1, 2 or 3 substituents, the substituents being identical or different and denoting halogen, trifluoromethyl, $C_1$–$C_4$ alkyl or $C_1$–$C_4$ alkoxy, and, in formula (I) further, the $R_n$'s, independently of one another, denote halogen, trifluoromethyl, $C_1$–$C_8$ alkyl, $C_1$–$C_4$ alkoxy, $C_3$–$C_5$ alkenyl, $C_1$–$C_4$ alkoxycarbonyl, carboxyl, di-($C_1$–$C_4$)alkylaminomethyl or nitro, n is 0, 1, 2 or 3, or, in the event that n is 2, $R_n$ denotes a $C_4H_4$ radical which, together with the phenyl ring, forms a naphthyl ring, or, in the event that n is 1, $R_n$ represents a phenoxy group optionally carrying 1 or 2 substituents, the substituents being identical or different and denoting halogen, trifluoromethyl, $C_1$–$C_4$ alkyl, or $C_1$–$C_4$ alkoxy, $R_1$ denotes hydrogen, $C_1$–$C_4$ alkyl or a phenyl group optionally carrying 1 or 2 substituents, the substituents being identical or different and denoting halogen, trifluoromethyl, nitro, $C_1$–$C_4$ alkyl or $C_1$–$C_4$ alkoxy, m denotes 0, 1 or 2, and Z denotes either (a) an amino radical of the formula Z(a)

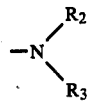

in which $R_2$ and $R_3$ are identical or different and each denotes hydrogen, $C_1$–$C_8$ alkyl, $C_3$–$C_5$ alkenyl, $C_3$–$C_8$ cycloalkyl or a phenyl or benzyl group optionally carrying 1, 2 or 3 substituents, the substituents being identical or different and each denoting halogen, $C_1$–$C_4$ alkyl, $C_1$–$C_4$ alkoxy or trifluoromethyl, or one of the two radicals $R_2$ or $R_3$ denotes $C_1$–$C_5$ alkanoyl or $C_1$–$C_4$ alkoxycarbonyl, or (b) a radical of the formula Z(b)

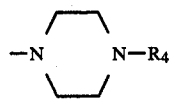

in which $R_4$ denotes hydrogen, $C_1$–$C_4$ alkyl, $C_3$–$C_5$ alkenyl, hydroxy-($C_2$–$C_3$)-alkyl, $C_1$–$C_4$-alkoxy-($C_2$–$C_3$)-alkyl, $C_1$–$C_5$ alkanoyl, $C_2$–$C_5$ alkanoylmethyl, $C_1$–$C_4$ alkylsulfonyl, $C_1$–$C_4$ alkyloxycarbonyl, $C_1$–$C_4$ alkyloxycarbonylmethyl, mono-($C_1$–$C_4$)-alkylaminocarbonylmethyl, di-($C_1$–$C_4$)-alkylaminocarbonylmethyl, aminocarbonylmethyl, mono-($C_1$–$C_4$)alkylaminocarbonyl, di-($C_1$–$C_4$)-alkylaminocarbonyl, $C_1$–$C_4$-alkylaminothiocarbonyl, $C_1$–$C_4$-alkylthiothiocarbonyl, aminocarbonyl, $C_3$–$C_5$-alkenylaminocarbonyl, or $C_3$–$C_5$-alkenylaminothiocarbonyl, or $R_4$ denotes a phenyl, phenylmethyl, phenylaminocarbonyl or benzoyl group, each of the phenyl groups optionally carring 1 or 2 substituents which are identical or different and denote halogen, trifluoromethyl, $C_1$–$C_4$-alkyl, or $C_1$–$C_4$-alkoxy, or (c) a 1-H-imidazol-1-yl, 1H-1,2,4-triazol-1-yl, pyrazol-1-yl-, pyrrolidin-1-yl-, piperidin-1-yl-, morpholin-4-yl, thiomorpholin-4-yl, 2,6-dimethylmorpholin-4-yl, 2,6-dimethylthiomorpholin-4-yl, 1,2,3,4-tetrahydroquinolin-1-yl or 1,2,3,4-tetrahydroisoquinolin-2-yl radical, or (d) an isocyano group of the formula Z(d)

or (e) an isothiocyano group of the formula Z(e)

or (f) a radical of the general formula Z(f)

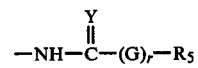

in which Y represents oxygen or sulfur, G represents oxygen or an NH group, r represents 0 or 1 and R$_5$ represents hydrogen, C$_1$–C$_4$-alkyl, monohalogenomethyl, dihalogenomethyl, trihalogenomethyl or a phenyl group optionally carrying 1 or 2 substituents, the substituents being identical or different and each denoting halogen, trifluoromethyl, C$_1$–C$_4$ alkyl, or C$_1$–C$_4$ alkoxy, subject to the proviso that, in the event that Y represents a sulfur atom, G denotes an NH group and r denotes the number 1, that, in the event that G represents an oxygen atom and r represents the number 1, R$_5$ does not denote hydrogen, and that, in the event that R$_5$ represents monohalogenomethyl, dihalogenomethyl or trihalogenomethyl, r denotes 0 and Y denotes oxygen.

2. A 1-(1,3-dioxolan-2-ylmethyl)-azole of the formula (I) as claimed in claim 1 and its stereoisomers and its salts with physiologically acceptable acids, in which D denotes a 1-(1,3-dioxolan-2-ylmethyl)-azole radical as given in claim 1, in which A denotes methine and X denotes 4-fluorophenyl, 4-chlorophenyl, 4-bromophenyl, 4-trifluoromethyl or 2,4-dichlorophenyl and, in formula (I) further, the R$_n$'s, independently of one another, denote halogen, C$_1$–C$_4$-alkyl, methoxy, allyl, n is 0 or 2, R$_1$ denotes hydrogen, m denotes 0 and Z denotes either (a) an amino radical of the formula Z(a)

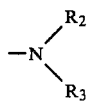

in which R$_2$ and R$_3$ are identical or different and denote hydrogen, C$_1$–C$_8$-alkyl, allyl, C$_3$–C$_8$-cycloalkyl or a phenyl or benzyl group optionally carrying 1 or 2 substituents, the substituents being identical or different and each denoting halogen, C$_1$–C$_4$-alkyl, C$_1$–C$_4$-alkoxy or trifluoromethyl, or one of the two radicals R$_2$ or R$_3$ denotes C$_1$–C$_5$-alkanoyl, or (b) a radical of the formula Z(b)

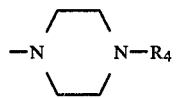

in which R$_4$ denotes hydrogen, C$_1$–C$_4$-alkyl, allyl, C$_1$–C$_5$-alkanoyl, methylsulfonyl, methoxycarbonyl, or C$_1$–C$_4$-alkylaminocarbonyl or R$_4$ denotes a phenyl, phenylmethyl, or benzoyl group, each of the phenyl groups optionally carrying 1 or 2 substituents which are identical or different and denote halogen, trifluoromethyl, C$_1$–C$_4$-alkyl, or C$_1$–C$_4$-alkoxy, or (c) a piperidin-1-yl-, morpholin-4-yl,2,6-dimethylmorpholin-4-yl, thiomorpholin-4-yl-, 2,6-dimethylthiomorpholin, (d) a radical of the formula Z(f)

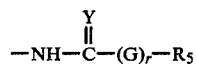

in which Y represents oxygen, r represents 0, and R$_5$ represents C$_1$–C$_4$-alkyl, or a phenyl group optionally carrying 1 or 2 substituents, the substituents being identical or different and each denoting halogen, trifluoromethyl, C$_1$–C$_4$-alkyl, or C$_1$–C$_4$-alkoxy.

3. 2-S, (R)-(2,4-dichlorophenyl)-2-(imidazol-1-ylmethyl)-4-R, (S)-[4-(4-chlorobenzoylaminomethyl)-2,6-dimethylphenoxymethyl]-1,3-dioxolan.

4. 2-S, (R)-(2,4-dichlorophenyl)-2-(imidazol-1-ylmethyl)-4-R, (S)-[4-(morpholin-4-ylmethyl)-phenoxymethyl]-1,3-dioxolan.

5. 2-S, (R)-(2,4-dichlorophenyl)-2-(imidazol-1-ylmethyl)-4-R, (S)-[4-(N-octylaminomethyl)-phenoxymethyl]-1,3-dioxolan.

6. 2-S, (R)-(2,4-dichlorophenyl)-(2-imidazol-1-ylmethyl)-4-R, (S)-[4-(4-acetylpiperazin-1-ylmethyl)-phenoxymethyl]-1,3-dioxolan.

7. 2-S, (R)-(2,4-dichlorophenyl)-2-(imidazol-1-ylmethyl)-4-R, (S)-[2,6-dimethyl-4-(N,N-dimethylaminomethyl)-phenoxymethyl]-1,3-dioxolan.

8. 2-S, (R)-(2,4-dichlorophenyl)-2-(imidazol-1-ylmethyl)-4-R, (S)-[2,6-dimethyl-4-(2,6-dimethylmorpholin-4-ylmethyl)-phenoxymethyl]-1,3-dioxolan.

9. 2-S, (R)-(2,4-dichlorophenyl)-2-(imidazol-1-ylmethyl)-4-R, (S)-[2-chloro-4-(2,6-dimethylmorpholin-4-ylmethyl)-6-methyl-phenoxymethyl]-1,3-dioxolan.

10. 2-S, (R)-(2,4-dichlorophenyl)-2-(imidazol-1-ylmethyl)-4-R, (S)-[2,6-dimethyl-4-(2,6-dimethylthiomorpholin-4-ylmethyl)-phenoxymethyl]-1,3-dioxolan.

11. 2-S, (R)-(2,4-dichlorophenyl)-2-(imidazol-1-ylmethyl)-4-R, (S)-[2,6-dimethyl-4-(n-octylaminomethyl)-phenoxymethyl]-1,3-dioxolan.

12. A pharmaceutical composition which contains a compound according to claim 1 in admixture or conjunction with a pharmaceutically acceptable carrier.

13. Method of treating patients suffering from mycoses, protozoa, Gram-positive or Gram-negative bacteria by administering an effective amount of a compound of formula I as claimed in claim 1.

* * * * *